(12) United States Patent
Fleiszig et al.

(10) Patent No.: US 9,187,541 B2
(45) Date of Patent: Nov. 17, 2015

(54) ANTI-MICROBIAL PEPTIDES AND METHODS OF USE THEREOF

(75) Inventors: Suzanne M. J. Fleiszig, Oakland, CA (US); David J. Evans, Oakland, CA (US); Kwai Ping Tam, Oakland, CA (US); James J. Mun, Richmond, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/111,152

(22) PCT Filed: Apr. 16, 2012

(86) PCT No.: PCT/US2012/033759
§ 371 (c)(1),
(2), (4) Date: Jan. 22, 2014

(87) PCT Pub. No.: WO2012/148720
PCT Pub. Date: Nov. 1, 2012

(65) Prior Publication Data
US 2014/0221273 A1   Aug. 7, 2014

Related U.S. Application Data

(60) Provisional application No. 61/479,507, filed on Apr. 27, 2011.

(51) Int. Cl.
| | |
|---|---|
| *A61K 38/00* | (2006.01) |
| *C07K 14/47* | (2006.01) |
| *A61P 31/04* | (2006.01) |
| *A01N 63/00* | (2006.01) |
| *C07K 7/06* | (2006.01) |
| *C07K 7/08* | (2006.01) |

(52) U.S. Cl.
CPC ............ *C07K 14/4741* (2013.01); *A01N 63/00* (2013.01); *C07K 7/06* (2013.01); *C07K 7/08* (2013.01)

(58) Field of Classification Search
CPC ........ C07K 14/4741; C07K 7/06; C07K 7/08; A01N 63/00
See application file for complete search history.

(56) References Cited

U.S. PATENT DOCUMENTS

| | | |
|---|---|---|
| 5,202,420 A | 4/1993 | Zasloff et al. |
| 6,482,799 B1 | 11/2002 | Tuse et al. |
| 2003/0064419 A1* | 4/2003 | Chandrasiri Herath et al. ............ 435/7.23 |
| 2008/0274165 A1 | 11/2008 | Van Dyke |
| 2009/0053831 A1* | 2/2009 | Hornbeck et al. ............ 436/536 |
| 2010/0159006 A1 | 6/2010 | Schmidtchen et al. |
| 2011/0070276 A1 | 3/2011 | Cowsar |
| 2012/0021033 A1 | 1/2012 | Kaplan |

FOREIGN PATENT DOCUMENTS

WO   WO2008/022444   2/2008

OTHER PUBLICATIONS

Water, from http://www.biology-online.org/dictionary/Water, pp. 1-3, accessed Apr. 24, 2014.*
Natural dyes, from http://pioneerthinking.com/crafts/natural-dyes, pp. 1-13, accessed Jan. 27, 2015.*
Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Smales, C. Mark and James, David C. Therapeutic proteins, methods and protocols, Humana press, 2005, enclosed pp. 1-2.*
Angus et al., "The ADP-ribosylation domain of pseudomonas aeruginosa ExoS is required for membrane bleb niche formation and bacterial survival within epithelial cells", Infection and Immunity, Nov. 2010, 78(11):4500-4510.
Augustin et al., "Role of defensins in corneal epithelial barrier function against pseudomonas aeruginosa traversal", Infection and Immunity, Feb. 2011, 79(2):595-605.

* cited by examiner

*Primary Examiner* — Julie Ha
*Assistant Examiner* — Li Ni Komatsu
(74) *Attorney, Agent, or Firm* — Bozicevic Field & Francis, LLP; Paula A. Borden; Kyle A. Gurley

(57) ABSTRACT

The present disclosure provides antimicrobial peptides, and compositions comprising same. The present disclosure further provides methods of inhibiting microbial growth.

20 Claims, 21 Drawing Sheets

| Peptide | Amino Acid Sequence | Predicted Hydrophobic Face | Predicted Secondary Structure | Possible Trans-membrane Helix | pI | Net Charge at pH 7.0 | Hydrophobic Moment (μH) |
|---|---|---|---|---|---|---|---|
| 18mer-N | AIGGGLSSVGGGSSTIKY (SEQ ID NO:2) | AGGIVI (SEQ ID NO:64) | Coil | Yes | 8.63 | +1 | 0.238 |
| 18mer-C | RAIGGGLSSVGGGSSTIK (SEQ ID NO:3) | AGGIVI (SEQ ID NO:64) | Coil | Yes | 11.0 | +2 | 0.348 |
| 17mer | AIGGGLSSVGGGSSTIK (SEQ ID NO:1) | - | Coil | Yes | 8.80 | +1 | 0.309 |
| 14mer | GGLSSVGGGSSTIK (SEQ ID NO:4) | - | Coil | No | 8.75 | +1 | 0.252 |
| 13mer | AIGGGLSSVGGGS (SEQ ID NO:5) | - | Coil | No | 5.57 | 0 | 0.325 |

FIG. 1g

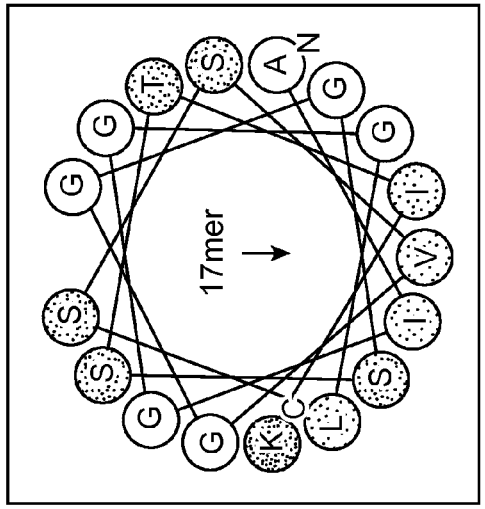
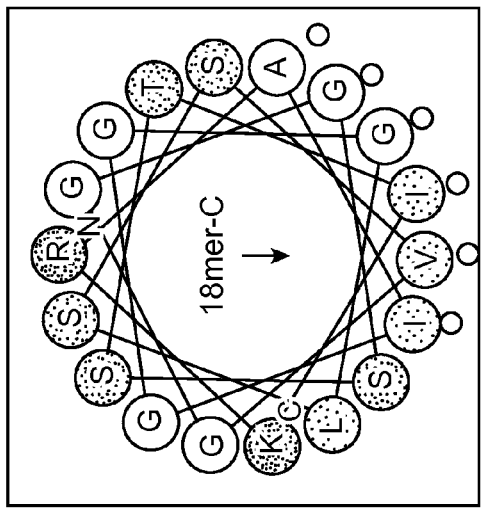
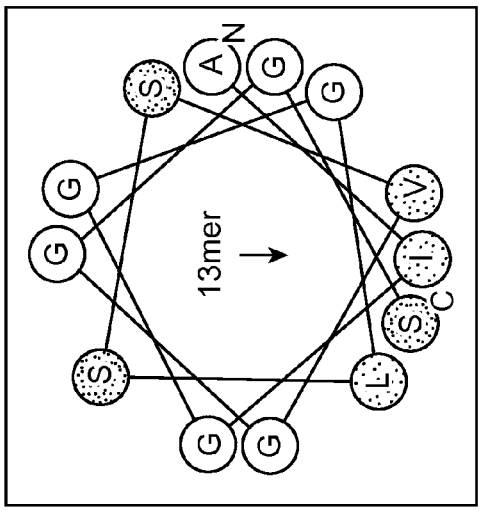
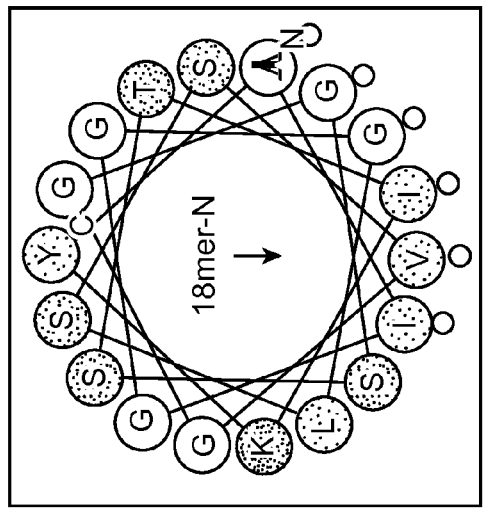
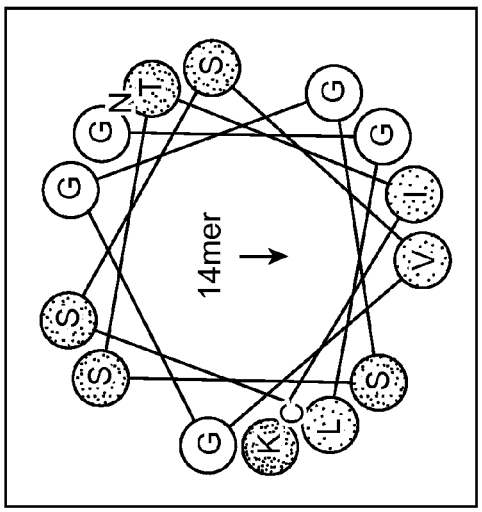
FIG. 1h

| Peptide | Amino Acid Sequence | Predicted Hydrophobic Face | Predicted Secondary Structure | Possible Trans-membrane Helix | pI | Net Charge at pH 7.0 | Hydrophobic Moment (μH) |
|---|---|---|---|---|---|---|---|
| 19mer | RAIGGGLSSVGGGSSTIKY (SEQ ID NO:6) | AGGIVI (SEQ ID NO:64) | Coil | Yes | 9.99 | +2 | 0.279 |
| 36mer | YGSGLGVGGGFSSSSG RAIGGGLSSVGGGSSTIKYT (SEQ ID NO:8) | - | Coil | Yes | 9.70 | +2 | 0.219 |
| 10mer | GGLSSVGGGS (SEQ ID NO:9) | - | Coil | No | 5.52 | 0 | 0.255 |

(SEQ ID NO:70)

(SEQ ID NO:71)
(SEQ ID NO:72)

(SEQ ID NO:73)

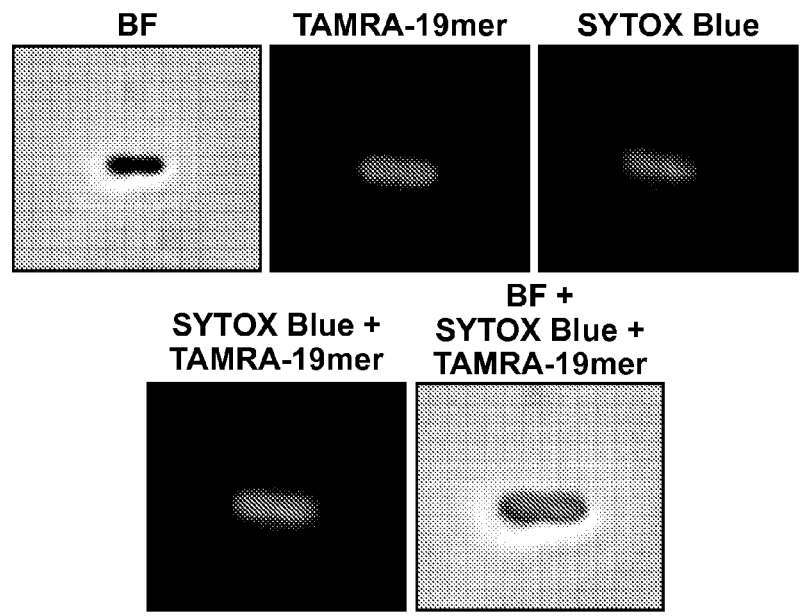
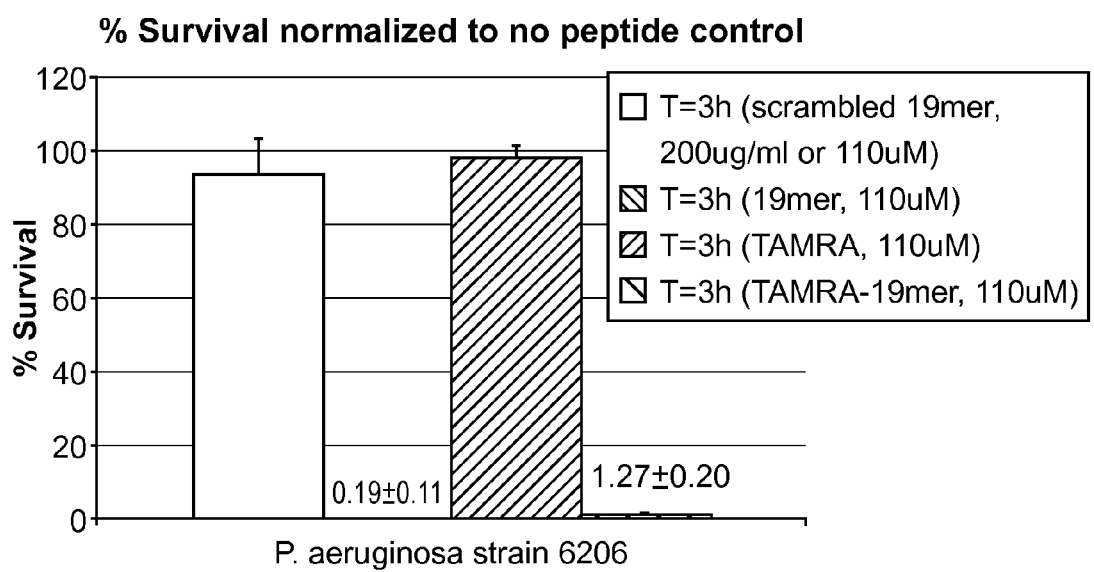
FIG. 3a

GenBank AAI25059
*Homo sapiens* keratin 6A (564 amino acids)

```
  1 maststtirs hsssrrgfsa nsarlpgvsr sgfssvsvsr srgsgglgga cggagfgsrs
 61 lyglggskri sigggscais ggygsraggs ygfggagsgf gfgggagigf glgggaglag
121 gfgppgfpvc ppggiqevtv nqslltplnl qidptiqrvr aeereqiktl nnkfasfidk
181 vrfleqqnkv letkwtllqe qgtktvrqnl eplfeqyinn lrrqldsivg ergrldselr
241 gmqdlvedfk nkyedeinkr taaenefvtl kkdvdaaymn kvelqakadt ltdeinflra
301 lydaelsqmq thisdtsvvl smdnnrnldl dsiiaevkaq yeeiaqrsra eaeswyqtky
361 eelqvtagrh gddlrntkqe iaeinrmiqr lrseidhvkk qcanlqaaia daeqrgemal
421 kdaknklegl edalqkakqd larllkeyqe lmnvklaldv eiatyrklle geecrlngeg
481 vgqvnisvvq stvssgygga sgvgsglglg ggssysygsg lgvgggfsss sgraigggls
541 svgggsstik ytttssssrk sykh
```

ANTI-MICROBIAL PEPTIDES AND METHODS OF USE THEREOF

CROSS-REFERENCE

This application is a national stage filing under 35 U.S.C. §371 of PCT/US2012/033759, filed Apr. 16, 2012, which claims the benefit of U.S. Provisional Patent Application No. 61/479,507, filed Apr. 27, 2011, which applications are incorporated herein by reference in their entirety.

STATEMENT REGARDING FEDERALLY SPONSORED RESEARCH

This invention was made with government support under Grant No. R01-EY011221 awarded by the National Institutes of Health. The government has certain rights in the invention.

BACKGROUND

Exposed tissue surfaces, including skin and mucosa, are lined with multilayers of epithelial cells. Among their functions, they form a barrier to prevent microbe penetration. Significant effort has focused on understanding how epithelial cells participate in immune responses when infectious disease occurs, or during other forms of tissue challenge.

Keratin proteins are an extremely diverse and ancient class of biomolecule. Previous studies of keratins have focused on mechanical, structural and architectural functions of keratins, their roles in intracellular signaling, and changes to expression in certain diseases.

There is a need in the art for antimicrobial agents, e.g., agents that inhibit growth of microbes that infect epithelial cells.

LITERATURE

U.S. Patent Publication No. 2011/0070276

SUMMARY

The present disclosure provides antimicrobial peptides, and compositions comprising same. The present disclosure further provides methods of inhibiting microbial growth.

BRIEF DESCRIPTION OF THE DRAWINGS

FIG. 1A-1H depict detection of keratin 6A-derived peptides in <3 kDa and 3-10 kDa antimicrobial fractions of human corneal epithelial cell lysates. (FIG. 1H) Helical wheel presentations of peptide sequences listed in FIG. 1G. For example, upper left presentation depicts the sequence "18mer-N" (SEQ ID NO:1). SEQ ID NO:65 labelled underneath the presentation is derived by reading amino acid sequence counter-clockwise from the amino acid labelled "N".

(FIG. 2B) Helical wheel presentations of peptide sequences. For example, bottom left presentation depicts the sequence "19mer" (SEQ ID NO:6) listed in above table. SEQ ID NO:70 labelled underneath the presentation is derived in the same way as described for FIG. 1H.

FIG. 3A-3B depict binding of a keratin-derived 19-mer to bacterial cells and permeabilization of the bacterial cell membrane.

FIG. 5 depicts an amino acid sequence of human keratin 6A (SEQ ID NO:57).

DEFINITIONS

Figure 1A:
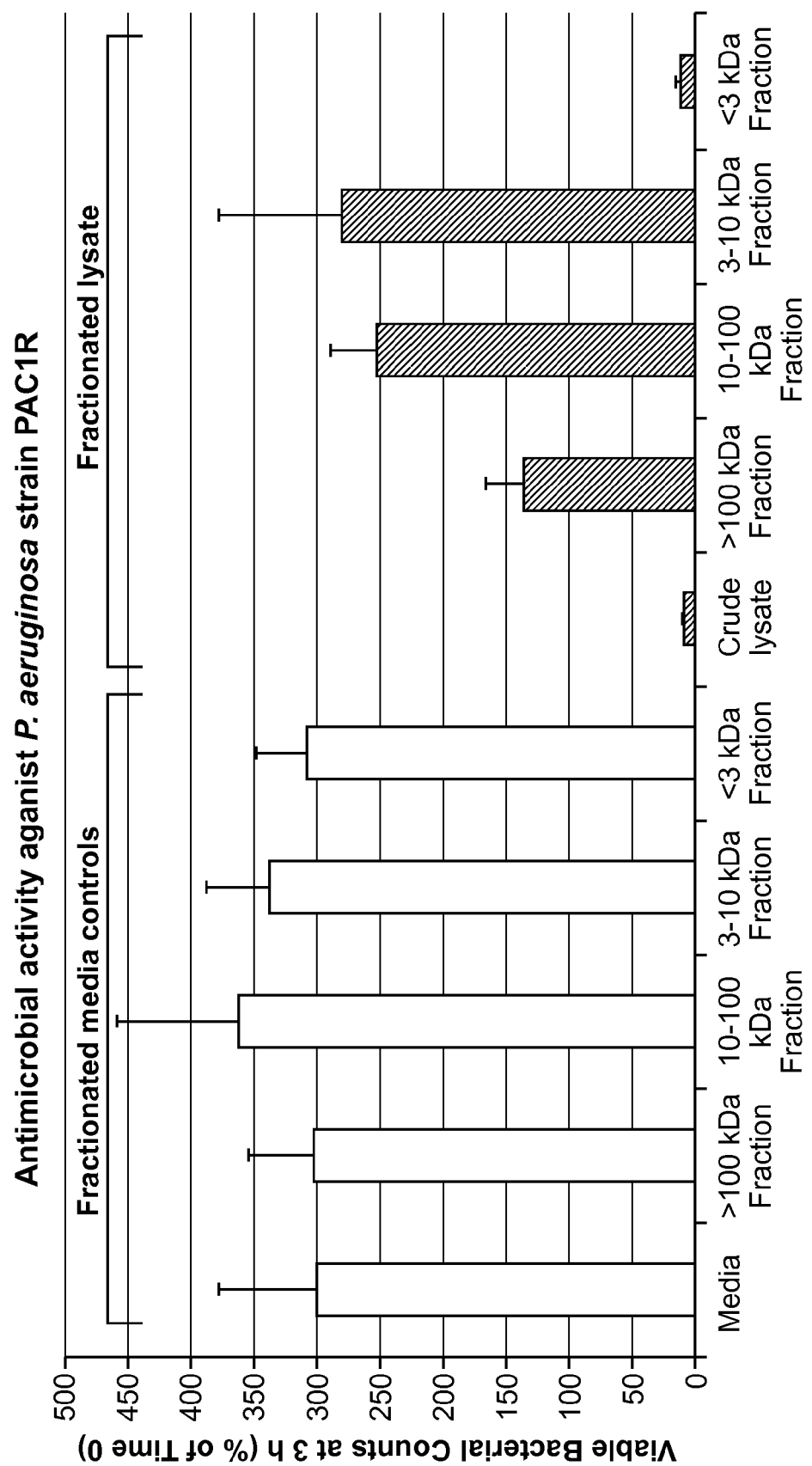

The terms "polypeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "nucleic acid molecule" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

"Isolated" refers to a peptide of interest that, if naturally occurring, is in an environment different from that in which it may naturally occur. "Isolated" is meant to include peptides that are within samples that are substantially enriched for the peptide of interest and/or in which the peptide of interest is partially or substantially purified. Where the peptide is not naturally occurring, "isolated" indicates the peptide has been separated from an environment in which it was made by either synthetic or recombinant means.

"Substantially pure" indicates that an entity (e.g., a keratin-derived antimicrobial peptide) makes up greater than about 50% of the total content of the composition (e.g., total protein of the composition), or greater than about 80% of the total protein content. For example, a "substantially pure" peptide refers to compositions in which at least 80%, at least 85%, at least 90% or more of the total composition is the peptide (e.g. 95%, 98%, 99%, greater than 99% of the total protein). The peptide can make up greater than about 90%, or greater than about 95% of the total protein in the composition.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an anti-microbial peptide" includes a plurality of such peptides and reference to "the formulation" includes reference to one or more formulations and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides antimicrobial peptides, and compositions, including pharmaceutical compositions, comprising the peptides. The present disclosure further provides a medical device comprising a subject peptide. The present disclosure further provides methods of inhibiting microbial growth.

Anti-Microbial Peptides

The present disclosure provides peptides having anti-microbial activity, e.g., can inhibit growth of a bacterium that is a human pathogen. A subject anti-microbial peptide is isolated, and in many instances is purified, i.e., substantially pure. In some cases, a subject anti-microbial peptide is synthetic, e.g., made in a laboratory by chemical synthesis methods or by recombinant methods.

A subject anti-microbial peptide has sequence similarity to a carboxyl-terminal portion of human keratin 6A. A subject anti-microbial peptide can comprise an amino acid sequence having at least about 80%, at least about 85%, at least about 90%, at least about 95%, at least about 98%, at least about 99%, or 100%, amino acid sequence identity to a contiguous stretch of from about 10 amino acids to 550 amino acids (e.g., a contiguous stretch of from about 10 amino acids (aa) to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, from about 100 aa to about 200 aa, from about 200 aa to about 300 aa, from about 300 aa to about 400 aa, from about 400 aa to about 500 aa, or from about 500 aa to 550 aa) of the amino acid sequence depicted in FIG. 5 (SEQ ID NO:57).

A subject synthetic anti-microbial peptide can have a length of from about 10 amino acids to about 10 amino acids to about 550 amino acids, e.g., from about 10 amino acids (aa) to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, from about 100 aa to about 200 aa, from about 200 aa to about 300 aa, from about 300 aa to about 400 aa, from about 400 aa to about 500 aa, or from about 500 aa to 550 aa.

In some embodiments, a subject anti-microbial peptide has a length of from about 10 amino acids to about 50 amino acids. In some embodiments, a subject anti-microbial peptide has a length of 10 amino acids (aa), 11 aa, 12 aa, 13 aa, 14 aa, 15 aa, 16 aa, 17 aa, 18 aa, 19 aa, 20 aa, 21 aa, 22, aa 23 aa, 24 aa, 25, aa, 26 aa, 27 aa, 28 aa, 29 aa, 30 aa, 31 aa, 32 aa, 33 aa, 34 aa, 35 aa, 36 aa, 37 aa, 38 aa, 39 aa, 40 aa 41 aa, 42 aa, 43 aa, 44 aa, 45 aa, 46 aa, 47 aa, 48 aa, 49 aa, or 50 aa.

An anti-microbial peptide of the present disclosure can be derived from amino acids 1-50, amino acids 51-100, amino acids 101-150, amino acids 151-200, amino acids 201 to 250, amino acids 251-300, amino acids 301-350, amino acids 351-400, amino acids 401-450, amino acids 451-500, or amino acids 501-559 of the human keratin 6A amino acid sequence depicted in FIG. 5 (SEQ ID NO:57).

An anti-microbial peptide of the present disclosure can be derived from amino acids 515 to 559 of the human keratin 6A amino acid sequence depicted in FIG. 5. A subject anti-microbial peptide can comprise an amino acid sequence having at least about 80%, at least about 85%, at least about 90%, at least about 95%, at least about 98%, at least about 99%, or 100%, amino acid sequence identity to a contiguous stretch of from about 10 to about 45 amino acids of amino acids 515 to 559 of the amino acid sequence depicted in FIG. 5.

A subject anti-microbial peptide can have one or more of the following features: a +2 charge at pH 7.0; a hydrophobicity moment of about 0.279 µH; and a coil structure.

In some cases, a subject antimicrobial peptide has a length of from about 10 amino acids to about 50 amino acids; and comprises an amino acid sequence having at least about 90% amino acid sequence identity to a contiguous stretch of from about 10 amino acids to about 35 amino acids of the sequence

```
                                                    (SEQ ID NO: 63)
YSYGSGLGVGGGFSSSSGRAIGGGLSSVGGGSSTIKYTTTSSSSR;
```

As non-limiting examples, a subject anti-microbial peptide can comprise one of the following amino acid sequences:

```
                                                    (SEQ ID NO: 1)
    AIGGGLSSVGGGSSTIK;

(SEQ ID NO: 2)
    AIGGGLSSVGGGSSTIKY;

(SEQ ID NO: 3)
    RAIGGGLSSVGGGSSTIK;
```

-continued

GGLSSVGGGSSTIK; (SEQ ID NO: 4)

AIGGGLSSVGGGS; (SEQ ID NO: 5)

RAIGGGLSSVGGGSSTIKY; (SEQ ID NO: 6)

YGSGLGVGGGFSSSSGRAIGGGLSSVGGGSSTIKY; (SEQ ID NO: 7)

YGSGLGVGGGFSSSSGRAIGGGLSSVGGGSSTIKYT; (SEQ ID NO: 8)

GGLSSVGGGS; (SEQ ID NO: 9)

GSGLGVGGGFSSSSGRAIGGGLSSVGGGSSTIK; (SEQ ID NO: 10)

GSGLGVGGGFSSSSGRAIGGGLSSVGGGSSTIKY; (SEQ ID NO: 11)

SGLGVGGGFSSSSGRAIGGGLSSVGGGSSTIK; (SEQ ID NO: 12)

SGLGVGGGFSSSSGRAIGGGLSSVGGGSSTIKY; (SEQ ID NO: 13)

GLGVGGGFSSSSGRAIGGGLSSVGGGSSTIK; (SEQ ID NO: 14)

GLGVGGGFSSSSGRAIGGGLSSVGGGSSTIKY; (SEQ ID NO: 15)

LGVGGGFSSSSGRAIGGGLSSVGGGSSTIK; (SEQ ID NO: 16)

LGVGGGFSSSSGRAIGGGLSSVGGGSSTIKY; (SEQ ID NO: 17)

GVGGGFSSSSGRAIGGGLSSVGGGSSTIK; (SEQ ID NO: 18)

GVGGGFSSSSGRAIGGGLSSVGGGSSTIKY; (SEQ ID NO: 19)

VGGGFSSSSGRAIGGGLSSVGGGSSTIK; (SEQ ID NO: 20)

VGGGFSSSSGRAIGGGLSSVGGGSSTIKY; (SEQ ID NO: 21)

GGGFSSSSGRAIGGGLSSVGGGSSTIK; (SEQ ID NO: 22)
and

GGGFSSSSGRAIGGGLSSVGGGSSTIKY. (SEQ ID NO: 23)

As further non-limiting examples, a subject anti-microbial peptide can comprise one of the following amino acid sequences:

LPGVSRSGFSS; (SEQ ID NO: 24)

GVSRSGFSSVSVSR; (SEQ ID NO: 25)

SGFSSVSVSR; (SEQ ID NO: 26)

SGFSSVSVSRS; (SEQ ID NO: 27)

SRGSGGLGGACGGAGFGS; (SEQ ID NO: 28)

GSGGLGGACGGAGFGS; (SEQ ID NO: 29)

GGAGFGSRSLYGLGGSK; (SEQ ID NO: 30)

SLYGLGGSKRISIGG; (SEQ ID NO: 31)

SLYGLGGSKRISIGGGS; (SEQ ID NO: 32)

AGGSYGFGGAGSGFG; (SEQ ID NO: 33)

AGGSYGFGGAGSGFGFGGGA; (SEQ ID NO: 34)

RNLDLDSIIAEVK; (SEQ ID NO: 35)

NLDLDSIIAEVK; (SEQ ID NO: 36)

YSYGSGLGVGGGFSSSSGR; (SEQ ID NO: 37)

YSYGSGLGVGGGFSSSSGRAIGGGLSSVGGGSSTIK; (SEQ ID NO: 38)

SYGSGLGVGGGFSSSSGR; (SEQ ID NO: 39)

YGSGLGVGGGFSSSSGR; (SEQ ID NO: 40)

YGSGLGVGGGFSSSSGRAIGGGLSSVGGGSSTIK; (SEQ ID NO: 41)

GSGLGVGGGFSSSSGR; (SEQ ID NO: 42)

GGFSSSSGRAIGGGLSSVGGGSSTIK; (SEQ ID NO: 43)

FSSSSGRAIGGGLSSVGGGSSTIK; (SEQ ID NO: 44)

SSSSGRAIGGGLSSVGGGSSTIK; (SEQ ID NO: 45)

SSSGRAIGGGLSSVGGGSSTIK; (SEQ ID NO: 46)

SSGRAIGGGLSSVGGGSSTIK; (SEQ ID NO: 47)

SGRAIGGGLSSVGGGSSTIK; (SEQ ID NO: 48)

GRAIGGGLSSVGGGSSTIK; (SEQ ID NO: 49)

AIGGGLSSVGGGSS; (SEQ ID NO: 50)

AIGGGLSSVGGGSST; (SEQ ID NO: 51)

AIGGGLSSVGGGSSTIKY; (SEQ ID NO: 52)

AIGGGLSSVGGGSSTIKYT; (SEQ ID NO: 53)

IGGGLSSVGGGSSTIK; (SEQ ID NO: 54)

GGGLSSVGGGSSTIK; (SEQ ID NO: 55)
and

VGGGSSTIKYTTTSSSSR. (SEQ ID NO: 56)

A subject anti-microbial peptide can comprise an amino acid sequence differing in amino acid sequence by one, two, three, four, or five amino acids, compared to any of the above-listed amino acid sequences. In other words, a subject anti-microbial peptide can comprise an amino acid sequence differing in amino acid sequence by one, two, three, four, or five amino acids, compared to a contiguous stretch of from about 10 to about 45 amino acids of amino acids 515 to 559 of the amino acid sequence depicted in FIG. 5.

A subject anti-microbial peptide can comprise one, two, or three amino acid substitutions (e.g., conservative amino acid substitutions), relative to a contiguous stretch of from about 10 amino acids to 559 amino acids (e.g., a contiguous stretch of from about 1 amino acids (aa) to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, from about 45 aa to about 50 aa, from about 50 aa to about 75 aa, from about 75 aa to about 100 aa, from about 100 aa to about 200 aa, from about 200 aa to about 300 aa, from about 300 aa to about 400 aa, from about 400 aa to about 500 aa, or from about 500 aa to 559 aa) of the amino acid sequence depicted in FIG. 5 A subject anti-microbial peptide can comprise one, two, or three amino acid substitutions (e.g., conservative amino acid substitutions), relative to a contiguous stretch of from about 10 to about 45 amino acids of amino acids 515 to 559 of the amino acid sequence depicted in FIG. 5.

By "conservative amino acid substitution" generally refers to substitution of amino acid residues within the following groups:
  1) L, I, M, V, F;
  2) R, K;
  3) F, Y, H, W, R;
  4) G, A, T, S;
  5) Q, N; and
  6) D, E.

Conservative amino acid substitutions in the context of a subject antimicrobial peptide are selected so as to preserve antimicrobial activity of the peptide. Such presentation may be preserved by substituting with an amino acid with a side chain of similar acidity, basicity, charge, polarity, or size to the side chain of the amino acid being replaced. Guidance for substitutions, insertion, or deletion may be based on alignments of amino acid sequences of different variant proteins or proteins from different species. For example, at certain residue positions that are fully conserved, substitution, deletion or insertion may not be allowed while at other positions where one or more residues are not conserved, an amino acid change can be tolerated. Residues that are semi-conserved may tolerate changes that preserve charge, polarity, and/or size.

In some cases, a subject anti-microbial peptide comprises one or more modifications. For example, a subject anti-microbial peptide can be cyclized. As another example, a subject anti-microbial peptide can have one or more amino acid modifications. A subject anti-microbial peptide can include one or more D-amino acids.

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are peptides that have phosphorylated amino acid residues, e.g. phosphotyrosine, phosphoserine, or phosphothreonine. In some instances, a subject anti-microbial peptide comprises one or more phosphorylated amino acids. In some instances, a subject anti-microbial peptide comprises one or more phosphotyrosine residues.

Also provided in the subject disclosure are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids.

The following are non-limiting examples of amino acid modifications that can be made to a subject antimicrobial peptide:

a) substitution of alkyl-substituted hydrophobic amino acids: including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids: including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains: including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids;

e) substitution of side chain amide residues: including asparagine, glutamine, and alkyl or aromatic substituted derivatives of asparagine or glutamine; and f) substitution of hydroxyl containing amino acids: including serine, threonine, homoserine, 2,3-diaminopropionic acid, and alkyl or aromatic substituted derivatives of serine or threonine.

In some cases, a subject antimicrobial peptide comprises one or more naturally occurring non-genetically encoded L-amino acids, synthetic L-amino acids or D-enantiomers of an amino acid. For example, a subject antimicrobial peptide can comprise only D-amino acids. For example, a subject antimicrobial peptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

In some cases, a subject antimicrobial peptide includes one or more linkages other than peptide bonds, e.g., at least two adjacent amino acids are joined via a linkage other than an amide bond. For example, to reduce or eliminate undesired proteolysis or other degradation pathways and/or to increase serum stability and/or to restrict or increase conformational flexibility, one or more amide bonds within the backbone of a subject antimicrobial peptide can be substituted.

For example, one or more amide linkages (—CO—NH—) in a subject antimicrobial peptide can be replaced with another linkage which is an isostere such as: —CH$_2$NH—, —CH$_2$S—, —CH$_2$CH$_2$—, —CH=CH-(cis and trans), —COCH$_2$—, —CH(OH)CH$_2$— and —CH$_2$SO—. This replacement can be made by methods known in the art.

As another example, one or more amide linkages in a subject antimicrobial peptide can be replaced with a reduced isostere pseudopeptide bond. Couder et al. (1993) *Int. J. Peptide Protein Res.* 41:181-184.

The protein may be joined to a wide variety of other oligopeptides or proteins for a variety of purposes. By providing for expression of the subject peptides, various post-translational modifications may be achieved. For example, by employing the appropriate coding sequences, one may provide farnesylation or prenylation. In this situation, the peptide will be bound to a lipid group at a terminus, so as to be able to be bound to a lipid membrane, such as a liposome.

A cysteine residue or a cysteine analog can be introduced into a subject antimicrobial peptide to provide for linkage to another peptide via a disulfide linkage or to provide for cyclization of a subject antimicrobial peptide. Methods of introducing a cysteine or cysteine analog are known in the art; see, e.g., U.S. Pat. No. 8,067,532.

A subject antimicrobial peptide can be cyclized. One or more cysteine or cysteine analogs can be introduced into a subject antimicrobial peptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moiety) that can form a cyclizing bond can be used and/or introduced. A cyclizing bond can be generated with any combination of amino acids (or with amino acid and —(CH$_2$)$_n$—CO— or —(CH$_2$)$_n$—C$_6$H$_4$—CO—) with functional groups which allow for the introduction of a bridge. Some examples are disulfides, disulfide mimetics such as the —(CH$_2$)$_n$— carba bridge, thioacetal, thioether bridges (cystathionine or lanthionine) and bridges containing esters and ethers.

Other modifications include, for example, an N-alkyl (or aryl) substitution (ψ[CONR]), or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

In some cases, one or more L-amino acids in a subject antimicrobial peptide is replaced with a D-amino acid.

In some cases, a subject antimicrobial peptide is a retroinverso analog. Sela and Zisman (1997) *FASEB J.* 11:449. Retro-inverso peptide analogs are isomers of linear peptides in which the direction of the amino acid sequence is reversed (retro) and the chirality, D- or L-, of one or more amino acids therein is inverted (inverso) e.g., using D-amino acids rather than L-amino acids. See, e.g., Jameson et al. (1994) *Nature* 368:744; and Brady et al. (1994) *Nature* 368:692.

The carboxyl group COR$_3$ of the amino acid at the C-terminal end of a subject antimicrobial peptide can be present in a free form (R$_3$=OH) or in the form of a physiologically tolerated alkaline or alkaline earth salt such as e.g. a sodium, potassium or calcium salt. The carboxyl group can also be esterified with primary, secondary or tertiary alcohols such as e.g., methanol, branched or unbranched C$_1$-C$_6$-alkyl alcohols, e.g., ethyl alcohol or tert-butanol. The carboxyl group can also be amidated with primary or secondary amines such as ammonia, branched or unbranched C$_1$-C$_6$-alkylamines or C$_1$-C$_6$ di-alkylamines, e.g., methylamine or dimethylamine.

The amino group of the amino acid NR$_1$R$_2$ at the N-terminus of a subject antimicrobial peptide can be present in a free form (R$_1$=H and R$_2$=H) or in the form of a physiologically tolerated salt such as e.g., a chloride or acetate. The amino group can also be acetylated with acids so that R$_1$=H and R$_2$=acetyl, trifluoroacetyl, or adamantyl. The amino group can be present in a form protected by conventional amino protecting groups of peptide chemistry such as e.g., Fmoc, Z, Boc, or Alloc. The amino group can be N-alkylated in which R$_1$ and/or R$_2$=C$_1$-C$_6$ alkyl or C$_2$-C$_8$ alkenyl or C$_7$-C$_9$ aralkyl.

Alkyl residues can be straight-chained, branched or optionally cyclic alkyl residues, e.g., methyl, ethyl, isopropyl and cyclohexyl.

One way to modify a subject antimicrobial peptide is to conjugate (e.g. link) one or more additional elements at the N- and/or C-terminus of the peptide, such as another protein (e.g. having an amino acid sequence heterologous to the subject peptide) and/or a carrier molecule. Thus, an exemplary protein can be provided as fusion proteins with a polypeptide(s) derived from a subject antimicrobial polypeptide.

Modifications that can enhance serum half-life of a subject antimicrobial peptide are of interest. A subject antimicrobial peptide may be "PEGylated", as containing one or more poly(ethylene glycol) (PEG) moieties. Methods and reagents suitable for PEGylation of a protein are well known in the art and may be found in U.S. Pat. No. 5,849,860, disclosure of which is incorporated herein by reference. PEG suitable for conjugation to a protein is generally soluble in water at room temperature, and has the general formula $R(O-CH_2-CH_2)_n O-R$, where R is hydrogen or a protective group such as an alkyl or an alkanol group, and where n is an integer from 1 to 1000. Where R is a protective group, it generally has from 1 to 8 carbons.

The PEG conjugated to the subject protein can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

Where a subject antimicrobial peptide is to be incorporated into a liposome, carbohydrate, lipid moiety, including N-fatty acyl groups such as N-lauroyl, N-oleoyl, fatty amines such as dodecyl amine, oleoyl amine, and the like (e.g., see U.S. Pat. No. 6,638,513) may also be used to modify the subject peptide.

Activity

An anti-microbial peptide of the present disclosure has anti-microbial activity (e.g., bactericidal activity) toward a number of bacteria that are human pathogens. For example, in some cases, a subject anti-microbial peptide can inhibit bacterial cell growth at a half-maximal effective concentration ($EC_{50}$) of from about 5 µg/ml to about 1 mg/ml, e.g., from about 5 µg/ml to about 10 µg/ml, from about 10 µg/ml to about 25 µg/ml, from about 25 µg/ml to about 50 µg/ml, from about 50 µg/ml to about 100 µg/ml, from about 100 µg/ml to about 250 µg/ml, from about 250 µg/ml to about 500 µg/ml, or from about 500 µg/ml to about 1 mg/ml. In some cases, a subject anti-microbial peptide can effect at least about 80%, at least about 85%, at least about 90%, at least about 95%, at least about 98%, at least about 99%, or greater than 99%, killing of a population of bacteria (bacteria that are human pathogens) at an $EC_{50}$ of from about 5 µg/ml to about 100 µg/ml.

In some cases, a subject anti-microbial peptide can reduce infection (e.g., invasion) of a human epithelial cell (e.g., a human corneal epithelial cell) by a bacterium by at least about 10%, at least about 15%, at least about 20%, at least about 25%, at least about 30%, at least about 40%, at least about 50%, at least about 60%, at least about 70%, at least about 80%, or more than 80%, compared to the level of infection by the bacterium in the absence of the peptide.

In some cases, a subject anti-microbial peptide can reduce bacteria-induced cytotoxicity of a human epithelial cell by at least about 10%, at least about 15%, at least about 20%, at least about 25%, at least about 30%, at least about 40%, at least about 50%, at least about 60%, at least about 70%, at least about 80%, or more than 80%, compared to the level of bacteria-induced cytotoxicity in the absence of the peptide.

An anti-microbial peptide of the present disclosure can have inhibitory activity toward various bacteria that are human pathogens, where such bacteria include, e.g., bacteria that are known to invade human epithelial cells. Bacteria that can be inhibited by a subject anti-microbial peptide include, e.g., members of Enterobacteriaciae; oxidase-positive Gram-negative bacteria; *Pseudomonas* spp.; *Burkholderia* spp.; *Vibrio* spp.; *Helicobacter* spp.; *Campylobacter* spp.; *Neisseria* spp.; *Acinetobacter* spp.; *Streptococcus* (e.g. B-G) etc.; Viridans Group Streptococci; Pneumococcus (*S. pneumoniae*); *Bacillus* spp.; *Clostridium* spp.; *Staphylococcus* spp.; and *Enterococcus* spp. Bacteria that can be inhibited by a subject anti-microbial peptide include, e.g., *Pseudomonas aeruginosa, Streptococcus pyogenes*, and the like.

Methods of Making an Anti-Microbial Peptide

A subject anti-microbial peptide can be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. In some cases, the compositions which are used will comprise at least 80% by weight of the desired product, at least about 85% by weight, at least about 95% by weight, or at least about 99.5% by weight, in relation to contaminants related to the method of preparation of the product and its purification. The percentages can be based upon total protein.

A subject peptide may be prepared by in vitro chemical synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like. For example, solid-phase peptide synthesis (SPPS) allows the incorporation of unnatural amino acids and/or peptide/protein backbone modification. Various forms of SPPS, such as Fmoc and Boc, are available for synthesizing a subject peptide. Details of the chemical synthesis are known in the art (e.g., Ganesan A. 2006 *Mini Rev. Med Chem.* 6:3-10 and Camarero J A et al. 2005 *Protein Pept Lett.* 12:723-8).

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Nucleic Acids

The present disclosure provides synthetic nucleic acids, where a subject synthetic nucleic acid comprises a nucleotide sequence encoding a subject anti-microbial peptide. A nucleotide sequence encoding a subject anti-microbial peptide can be operably linked to one or more regulatory elements, such as a promoter and enhancer, that allow expression of the nucleotide sequence in the intended target cells (e.g., a cell that is genetically modified to synthesize the encoded anti-microbial peptide. In some embodiments, a subject nucleic acid is a recombinant expression vector.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and the like.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein—Nucleic Acid Interaction.* Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) *Proc. Natl. Acad. Sci. U.S.A.* 80:21-25).

A nucleotide sequence encoding a subject anti-microbial peptide can be present in an expression vector and/or a cloning vector. An expression vector can include a selectable marker, an origin of replication, and other features that provide for replication and/or maintenance of the vector.

Large numbers of suitable vectors and promoters are known to those of skill in the art; many are commercially available for generating a subject recombinant construct. Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

The present disclosure provides isolated genetically modified host cells (e.g., in vitro cells) that are genetically modified with a subject nucleic acid. In some embodiments, a subject isolated genetically modified host cell can produce a subject anti-microbial peptide.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302.

Formulations

Anti-microbial peptides of the present disclosure can be incorporated into a variety of formulations for therapeutic use (e.g., inhibiting bacterial growth in vitro or in vivo). More particularly, a subject peptide can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, lotions, and aerosols. As such, administration of the compounds can be achieved in various ways, including oral, vaginal, buccal, rectal, parenteral, intraperitoneal, intradermal, transdermal, intratracheal, etc., administration. A subject peptide can be systemic after administration or may be localized by the use of an implant or other formulation that acts to retain the active dose at the site of implantation.

A subject formulation can include a pharmaceutically-acceptable salt of a subject anti-microbial peptide, where the anti-microbial peptide is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glutamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

A subject peptide can be administered alone, in combination with each other, or they can be used in combination with other known compounds (e.g., anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, a subject peptide can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral, vaginal or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. An implant containing a subject peptide is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific peptide, the severity of the symptoms and the susceptibility of the subject to side effects. Some of the specific peptides are more potent than others. Preferred dosages for a given peptide are readily determinable by those of skill in the art by a variety of means. One means is to measure the physiological potency of a given peptide.

Liposomes can be used as a delivery vehicle. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For preparing the liposomes, the procedure described by Kato et al (1991) J. Biol. Chem. 266:3361 may be used. Briefly, lipids and composition containing a subject peptide are combined in an appropriate aqueous medium, conveniently a saline medium where the total solids will be in the range of about 1-10 weight percent. After intense agitation for short periods of time, from about 5-60 seconds, the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Formulations with Other Active Agents

For use in the subject methods, a subject peptide may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; chloramphenicol; metronidazole; spectinomycin; trimethoprim; vancomycin; etc.

Coated Medical Devices

The present disclosure also provides a coated medical device, e.g., a coated implantable medical device or a coated insertable medical device, comprising a medical device having coated on at least one surface of the device a layer comprising a subject anti-microbial peptide. Suitable components of the layer comprising a subject anti-microbial peptide include, e.g., those described in U.S. Pat. No. 7,901,453; and U.S. Pat. No. 7,731,685. Coated implantable or insertable medical devices include, e.g., a urinary stent, a urinary catheter, a contact lens, an intraocular lens, an ophthalmic drug delivery device, and the like.

Disinfectant Compositions

The present disclosure provides disinfectant compositions comprising a subject anti-microbial peptide. For example, a subject composition comprising an anti-microbial peptide of the present disclosure can be a disinfectant composition, where such composition can be a hard surface cleaner composition. Hard surfaces that can be disinfected using a subject disinfectant composition include, e.g., hard surfaces in hospitals and other healthcare facilities; hard surfaces in the home (e.g., in the kitchen, in the bath, etc.); hard surfaces in educational facilities; hard surfaces in detention facilities; and industrial hard surfaces. Hard surfaces include, but are not limited to, ceramics, ceramic tile, grout, granite, concrete, minors, enameled surfaces, metals including aluminum, brass, stainless steel and the like. As such, a subject disinfectant composition can be formulated for use in educational facilities, healthcare facilities, etc., for hard surface disinfection of glazed tile, grout, porcelain, stainless steel, brass, finished wood and painted surfaces, polymeric surfaces, glass, and plastic.

A subject disinfectant composition can include, e.g., from about 0.5 weight % (wt. %) to about 20 wt. % of a subject anti-microbial peptide. A subject disinfectant composition can be provided as a liquid, a solid, a gel, etc.

A subject disinfectant composition can include, in addition to a subject anti-microbial peptide, one or more additional ingredients. Suitable additional ingredients include, but are not limited to, surfactants, chelating or complexing agents, pH adjusting agents, coloring agents (dyes), fragrances, foaming agents, and the like.

The pH of a subject disinfectant composition can range from about 5.0 to about 12.0, e.g., from about 5.0 to about 7.5, from about 7.5 to about 8.0, from about 8.0 to about 10.0, or from about 10.0 to about 12.0.

Suitable surfactants include, e.g., nonionic surfactants, amphoteric surfactants, anionic surfactants, and cationic surfactants. Suitable nonionic surfactants include, e.g., alkyl amine oxide, alkyl ether amine oxide, alkyl alcohol alkoxylates, aryl alcohol alkoxylates, substituted alcohol alkoxylates, block nonionic copolymers, heteric nonionic copolymers, alkanolamides, and polyethoxylated glycerol esters. Suitable amphoteric surfactants include, e.g., imidazolines and imidiazoline derivatives, isethionates, betaine derivatives, and amphoacetate derivatives. Suitable anionic surfactants include, e.g., sarcosine derivatives, succinic acid derivatives, carboxylated alcohols, alkyl sulfate and alkyl ether sulfates, sulfonic acid derivatives or diphenyl sulfonate derivatives, and alkyl aryl sulfonic acid derivatives. Suitable cationic surfactants include, e.g., quaternized polysaccharides, alkyl poly saccharides, alkoxylated amines, alkoxylated ether amine, phospholipids, and phospholipid derivatives.

In some embodiments, a subject antimicrobial composition includes a complexing agent. The complexing agent can include an inorganic complexing agent, an organic complexing agent, and mixtures thereof. Inorganic complexing agents include, but are not limited to, such compounds as sodium pyrophosphate, and sodium tripolyphosphate. Organic complexing agents include, but are not limited to, both polymeric and small molecule complexing agents. Small molecule organic complexing agents include aminocarboxylates such as acids or salts of ethylenediaminetetracetic acid (EDTA) and hydroxyethylenediaminetetracetic acid (HEDTA), diethylenetriaminepentaacetic acid (DTPA), nitrilotriacetic acid (NTA), methylglycinediacetic acid (MGDA), glutamic acid-N,N-diacetic acid, ethylenediaminesuccinic acid (EDDS), 2-hydroxyethyliminodiacetic acid (HEIDA), iminodisuccinic acid (IDS), 3-hydroxy-2,2'-iminodisuccinic acid (HIDS), hydroxymethyliminodiacetate (HIDA), ethylenediaminetetrapropionates, triethylenetetraminehexacetates, and the respective alkali metal, ammonium and substituted ammonium salts thereof. Phosphonates are also suitable for use as complexing agents in an anti-microbial composition of the present disclosure and include, but are not limited to ethylenediamine tetra(methylenephosphonate), nitrilotrismethylenephosphonate, diethylenetriaminepenta(methylene phosphonate), hydroxyethylidene diphosphonate (HEDP), isopropylmethylphosphonic acid (IMPA) and 2-phosphonobutane-1,2,4-tricarboxylic acid (PBTC).

Suitable fragrances include, e.g., terpenoids such as citronellol, aldehydes such as amyl cinnamaldehyde, a jasmine such as C1S-jasmine or jasmal, vanillin, and the like.

Wound and Surgical Dressings

The present disclosure provides materials for medical use, comprising a subject antimicrobial peptide. In some cases, the material is an article of manufacture, such as a wound dressing or a surgical dressing. The wound or surgical dressing can be a gauze, a bandage, a non-adhesive mesh, a membrane, or a tissue adhesive.

A subject wound or surgical dressing is configured to cover or surround a wound, a surgical incision, or any type of skin irritation. A subject wound or surgical dressing comprises a substrate configured to contact or surround a wound, a surgical site, or site of skin irritation. The substrate comprises a subject antimicrobial peptide in an amount effective to inhibit the growth of bacteria in or around a wound, surgical incision, or skin irritation.

A wound or surgical dressing can include surgical barriers, surgical adhesion barriers, membranes (e.g., barrier membranes), surgical sheets, surgical patches (e.g., dural patches), surgical wraps (e.g., vascular, perivascular, adventitial, periadventitital wraps, and adventitial sheets), meshes (e.g., perivascular meshes), bandages, liquid bandages, surgical dressings, gauze, fabrics, tapes, surgical membranes, polymer matrices, shells, envelopes, tissue coverings, and other types of surgical matrices, scaffolds, and coatings.

The wound or surgical dressing can include a backing, e.g., an outer layer, such as a flexible film; and can also comprise an adhesive portion for adhering to skin. The wound or surgical dressing may be secured into place by wrapping it onto itself (i.e., self-adhesive), or by securing it with sutures, staples, sealant, and the like. Alternatively, the wound or surgical dressing may adhere readily to tissue and therefore, additional securing mechanisms may not be required.

The substrate can comprise a gauze; an elastic material (e.g., a stretch-bonded laminate or a neck-bonded laminate); a coform web; an airlaid web; a bonded carded web; a wetlaid web; a foam; a film; a woven fabric; a knitted fabric; a hydroentangled web (e.g., comprising pulp fibers and synthetic fibers); and the like.

A subject wound or surgical dressing can be an adhesive bandage; a wrapping; or can be provided in any other suitable form.

A subject bacterial growth inhibitory peptide can be applied to any suitable wound or surgical dressing that is configured to contact or surround a wound, a surgical incision, or any skin irritation. When applied to a wound or surgical dressing, subject bacterial growth inhibitory peptide is bonded chemically or mechanically to a substrate on the dressing that is intended to contact a patient at or near the wound or surgical site. The substrate can be made from any suitable material. For example, subject bacterial growth inhibitory peptide may be bonded to a substrate made from natural materials or a substrate made from synthetic materials. For exemplary purposes, the following are some materials that may be used to bond with the bacteriostatic composition.

In some cases, the substrate comprises a polymer. The polymer may be a biodegradable polymer. Biodegradable compositions that may be used to prepare the mesh include polymers that comprise albumin, collagen, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, poly(caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of .epsilon.-caprolactone and lactide, copolymers of glycolide and .epsilon.-caprolactone, copolymers of lactide and 1,4-dioxane-2-one, polymers and copolymers that include one or more of the residue units of the monomers D-lactide, L-lactide, D,L-lactide, glycolide, .epsilon.-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids). These compositions include copolymers of the above polymers as well as blends and combinations of the above polymers. (see generally, Ilium, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986).

The substrate can comprise a biodegradable or resorbable polymer that is formed from one or more monomers selected from: lactide, glycolide, e-caprolactone, trimethylene carbonate, 1,4-dioxan-2-one, 1,5-dioxepan-2-one, 1,4-dioxepan-2-one, hydroxyvalerate, and hydroxybutyrate. The polymer can include, for example, a copolymer of a lactide and a glycolide. The polymer can include, for example, a poly(caprolactone). The polymer can include, for example, a poly(lactic acid), poly(L-lactide)/poly(D,L-Lactide) blends or copolymers of L-lactide and D,L-lactide. The polymer can include, for example, a copolymer of lactide and e-caprolactone. The polymer can include, for example, a polyester (e.g., a poly(lactide-co-glycolide). The poly(lactide-co-glycolide) may have a lactide:glycolide ratio ranges from about 20:80 to about 2:98, a lactide:glycolide ratio of about 10:90, or a lactide:glycolide ratio of about 5:95. In one aspect, the poly (lactide-co-glycolide) is poly(L-lactide-co-glycolide). Other examples of biodegradable materials include polyglactin, polyglycolic acid, autogenous, heterogenous, and xenogeneic tissue (e.g., pericardium or small intestine submucosa), and oxidized, regenerated cellulose. Such substrates can be knitted, woven or non-woven meshes. Examples of non-woven meshes include electrospun materials.

The substrate can be prepared from one or more non-biodegradable polymers. Representative examples of non-biodegradable compositions include ethylene-co-vinyl acetate copolymers, acrylic-based and methacrylic-based polymers (e.g., poly(acrylic acid), poly(methylacrylic acid), poly(methylmethacrylate), poly(hydroxyethylmethacrylate), poly(alkylcynoacrylate), poly(alkyl acrylates), poly(alkyl methacrylates)), polyolefins such as poly(ethylene) or poly (propylene), polyamides (e.g., nylon 6,6), poly(urethanes) (e.g., poly(ester urethanes), poly(ether urethanes), poly(carbonate urethanes), poly(ester-urea)), polyesters (e.g., PET, polybutyleneterephthalate, and polyhexyleneterephthalate), polyethers (poly(ethylene oxide), poly(propylene oxide), poly(ethylene oxide)-poly(propylene oxide) copolymers, diblock and triblock copolymers, poly(tetramethylene glycol)), silicone containing polymers and vinyl-based polymers (polyvinylpyrrolidone, poly(vinyl alcohol), poly(vinyl acetate phthalate), poly(styrene-co-isobutylene-co-styrene), fluorine containing polymers (fluoropolymers) such as fluorinated ethylene propylene (FEP) or polytetrafluoroethylene (e.g., expanded PTFE).

The substrate can comprise a combination of the above-mentioned biodegradable and non-degradable polymers. Further examples of polymers that may be used are either anionic (e.g., alginate, carrageenin, hyaluronic acid, dextran sulfate, chondroitin sulfate, carboxymethyl dextran, caboxymethyl cellulose and poly(acrylic acid)), or cationic (e.g., chitosan, poly-L-lysine, polyethylenimine, and poly(allyl amine)). Exemplary polymers (including copolymers and blends of these polymers) include poly(ethylene-co-vinyl acetate), poly(carbonate urethanes), poly(hydroxyl acids) (e.g., poly (D,L-lactic acid) oligomers and polymers, poly(L-lactic acid) oligomers and polymers, poly(D-lactic acid) oligomers and polymers, poly(glycolic acid), copolymers of lactic acid and glycolic acid, copolymers of lactide and glycolide, poly(caprolactone), copolymers of lactide or glycolide and ε-caprolactone), poly(valerolactone), poly(anhydrides), copolymers prepared from caprolactone and/or lactide and/or glycolide and/or polyethylene glycol.

Various commercially available substrates can be used in a subject wound or surgical dressing. Examples of substrates into which a subject antimicrobial peptide can be incorporated include INTERCEED (Johnson & Johnson, Inc.), PRECLUDE (W. L. Gore), and POLYACTIVE (poly(ether ester) multiblock copolymers (Osteotech, Inc., Shrewsbury, N.J.), based on poly(ethylene glycol) and poly(butylene terephthalate), and SURGICAL absorbable hemostat gauze-like sheet from Johnson & Johnson. Another suitable substrate is a prosthetic polypropylene mesh with a bioresorbable coating called SEPRAMESH Biosurgical Composite (Genzyme Corporation, Cambridge, Mass.). Also suitable is SEPRAFILM, (Genzyme Corp., Cambridge, Mass.), composed of modified hyaluronate and carboxymethylcellulose. Other suitable substrates include: (a) BARD MARLEX mesh (C.R. Bard, Inc.), which is a very dense knitted fabric structure with low porosity; (b) monofilament polypropylene mesh such as PROLENE available from Ethicon, Inc. Somerville, N.J. (see, e.g., U.S. Pat. Nos. 5,634,931 and 5,824,082)); (c) SURGISIS GOLD and SURGISIS IHM soft tissue graft (both from Cook Surgical, Inc.) which are devices specifically configured for use to reinforce soft tissue in repair of inguinal hernias in open and laparoscopic procedures; (d) thin walled polypropylene surgical meshes such as are available from Atrium Medical Corporation (Hudson, N.H.) under the trade names PROLITE, PROLITE ULTRA, and LITEMESH; (e) COMPOSIX hernia mesh (C.R. Bard, Murray Hill, N.J.), which incorporates a mesh patch (the patch includes two layers of an inert synthetic mesh, generally made of polypropylene, and is described in U.S. Pat. No. 6,280,453) that includes a filament to stiffen and maintain the device in a flat configuration; (f) VISILEX mesh (from C.R. Bard, Inc.), which is a polypropylene mesh that is constructed with monofilament polypropylene; (g) other meshes available from C.R. Bard, Inc. which include PERFIX Plug, KUGEL Hernia Patch, 3D MAX mesh, LHI mesh, DULEX mesh, and the VENTRALEX Hernia Patch; and (h) other types of polypropylene monofilament hernia mesh and plug products include HERTRA mesh 1, 2, and 2A, HERMESH 3, 4 & 5 and HERNIAMESH plugs T1, T2, and T3 from Herniamesh USA, Inc. (Great Neck, N.Y.).

Suitable substrates also include: a) the TRELEX NATURAL Mesh (Boston Scientific Corporation) which is composed of a unique knitted polypropylene material; b) the absorbable VICRYL (polyglactin 910) meshes (knitted and woven) and MERSILENE Polyester Fiber Mesh (Ethicon, Inc.); c) a mesh material formed from silicone elastomer known as SILASTIC Rx Medical Grade Sheeting (Platinum Cured) (Dow Corning Corporation); d) a mesh made from absorbable polyglycolic acid under the trade name DEXON Mesh Products (United States Surgical/Syneture (Norwalk, Conn.)); e) the CELGARD microporous polypropylene fiber and membrane (Membrana Accurel Systems (Obernburg, Germany)); f) a mesh material made from oxidized, regenerated cellulose known as INTERCEED TC7 (Gynecare Worldwide, a division of Ethicon, Inc.); g) DURAGEN PLUS Adhesion Barrier Matrix, which can be used as a barrier against adhesions following spinal and cranial surgery and for restoration of the dura mater (Integra LifeSciences Corporation (Plainsboro, N.J.); and h) HYDROSORB Shield from MacroPore Biosurgery, Inc. (San Diego, Calif.) is a film for temporary wound support to control the formation of adhesions in specific spinal applications.

Various substrates containing cellulosic material can be used in a subject wound or surgical dressing. For example, cellulosic materials are capable of forming chemical bonds with cationic materials having hydroxyl groups. Examples of cellulosic materials include gauze, wetlaid tissue webs, and airlaid webs.

Wetlaid tissue webs generally refer to tissue webs made from an aqueous suspension of cellulosic, namely pulp fibers. The pulp fibers may comprise, for instance, softwood fibers, hardwood fibers, and mixtures thereof. The wet pressed tissue product can generally be formed in any of a variety of processes known in the art. For example, the tissue web may be made through adhesive creping, wet creping, double creping, embossing, wet pressing, air pressing, through-air drying, creped through-air drying, uncreped through-air drying, as well as other steps known in the art.

Airlaid webs, on the other hand, are formed in an air forming process in which a fibrous nonwoven layer is created. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air or a spray adhesive. The production of airlaid nonwoven composites is well defined in the literature and documented in the art. Examples include the DanWeb process as described in U.S. Pat. No. 4,640,810 to Laursen et al. and assigned to Scan Web of North America Inc, the Kroyer process as described in U.S. Pat. No. 4,494,278 and U.S. Pat. No. 5,527,171, the method of U.S. Pat. No. 4,375,448, or other similar methods.

Other materials containing cellulosic fibers include coform webs and hydroentangled webs. In the coform process, at least one meltblown diehead is arranged near a chute through which other materials are added to a meltblown web while it is forming. Such other materials may be natural fibers, superabsorbent particles, natural polymer fibers (for example, rayon) and/or synthetic polymer fibers (for example, polypropylene or polyester), for example, where the fibers may be of staple length.

Coform processes are shown in commonly assigned U.S. Pat. No. 4,818,464 and U.S. Pat. No. 4,100,324, which are incorporated herein by reference. Webs produced by the coform process are generally referred to as coform materials. Natural fibers that may be combined with the meltblown fibers include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Acordis Cellulose Fibers Incorporated of Axis, Ala.

When containing cellulosic materials such as pulp fibers, a coform material may contain the cellulosic material in an amount from about 10% by weight to about 80% by weight, such as from about 30% by weight to about 70% by weight. For example, in one embodiment, a coform material may be produced containing pulp fibers in an amount from about 40% by weight to about 60% by weight.

Once a coform material is treated with a subject antimicrobial peptide in accordance with the present disclosure, in one embodiment, the peptide may bond to the cellulosic material contained within the coform material.

In addition to coform webs, hydroentangled webs can also contain synthetic and pulp fibers. Hydroentangled webs refer to webs that have been subjected to columnar jets of a fluid that cause the fibers in the web to entangle. Hydroentangling a web typically increases the strength of the web. In one embodiment, pulp fibers can be hydroentangled into a continuous filament material, such as a spunbond web. The hydroentangled resulting nonwoven composite may contain pulp fibers in an amount from about 50% to about 80% by weight, such as in an amount of about 70% by weight. Commercially available hydroentangled composite webs as described above are commercially available from the Kimberly-Clark Corporation under the name HYDROKNIT. Hydraulic entangling is described in, for example, U.S. Pat. No. 5,389,202, which is incorporated herein by reference.

In addition to the above substrates containing cellulosic fibers, other substrates that may be used in accordance with the present disclosure include synthetic webs. For instance, the substrate may comprise a meltblown web, a spunbond web, and laminates thereof.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited on a collecting surface.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

Laminates containing meltblown webs and spunbond webs include, for instance, meltblown/spunbond laminates and spunbond/meltblown/spunbond laminates.

In one embodiment, the synthetic webs may be elastic. As used herein, the terms "elastic" and "elastomeric" are generally used to refer to materials that, upon application of a force, are stretchable to a stretched, biased length which is at least about 125%, or one and one fourth times, unstretched length, and which will retract at least about 50% of its elongation upon release of the stretching, biasing force.

Elastic laminates that may be used as the substrate include, for instance, neck-bonded laminates and stretch-bonded laminates. As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992, 4,981,747, 4,965,122, and 5,336,545, all to Morman, all of which are incorporated herein by reference thereto.

As used herein, the term "stretch-bonded laminate" refers to a composite material having at least two layers in which one layer is a nonelastic gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415, which is incorporated herein by reference. Other composite elastic materials are described and disclosed in U.S. Pat. No. 4,789,699, U.S. Pat. No. 4,781,966, U.S. Pat. No. 4,657,802, and U.S. Pat. No. 4,655,760, all of which are incorporated herein by reference thereto.

In still another embodiment, the substrate may comprise a spunlace fabric. Spunlace fabrics are made according to a hydroentanglement process. The spunlace process subjects the fiber web to fine jets of water at high pressures. When the water streams contact the web, it repositions and entangles the fibers into an interlocked "spunlace" web. The web is then dried in hot ovens. Generally speaking, spunlace webs contain no chemical binders, and they have an excellent textile-like drape and softness; good mechanical and aesthetic properties, and good absorbency and wetting. A wide range of natural and synthetic fibers can be used to make spunlace webs, including polypropylene, Rayon, PET, and nylon. Staple fibers are also used in spunlace nonwovens products. Spunlace fabrics may include, for instance, a combination of rayon fibers and polyester fibers. The spunlaced fabrics may be creped or uncreped.

In still another embodiment, bonded carded webs may be used in the wound or surgical dressing as a substrate to bond to the bacteriostatic composition.

"Bonded carded webs" refer to webs which are made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

In still other embodiments, the substrate may comprise a foam, such as a polyurethane foam or a film. The film can be made from any suitable polymeric material. In still other embodiments, the substrate may comprise a woven fabric or a knitted fabric. The woven or knitted fabric may be made from natural fibers or synthetic fibers.

A subject antimicrobial peptide may be applied to the substrate using various methods. In some cases, the antimicrobial peptide is present in a composition is contained in a liquid carrier, such as water or a solvent and then applied to the substrate. For example, a subject antimicrobial peptide composition may be applied using traditional dip and squeeze techniques, where the substrate is dipped into the composition and excess liquids are squeezed off. In alternative embodiments, a bacterial growth inhibitory peptide composition may be applied to the substrate using brush coating, spraying, inkjet printing, and the like. It is also possible to add the bacteriostatic composition as an internal treatment to, for instance, a polymer fiber.

In another embodiment, a subject antimicrobial peptide composition may be first applied to a cellulosic material prior to incorporating the cellulosic material into a nonwoven web. For example, in one embodiment, the antimicrobial peptide composition may be combined with pulp fibers in an aqueous suspension prior to forming a tissue web. Alternatively, the antimicrobial peptide composition may be combined with the pulp fibers and then dried prior to being incorporated into an airlaid web, a coform web, or a hydroentangled web.

Methods of Inhibiting Bacterial Cell Growth

The present disclosure provides methods of inhibiting growth of a bacterium, e.g., a bacterium that is a human pathogen. A subject method of inhibiting bacterial growth can be carried out in vitro, e.g., to inhibit bacterial growth on a surface of a medical device, to inhibit bacterial growth in a liquid, in a cell culture, in a tissue in vitro, in a solid, or on the surface of a solid. A subject method of inhibiting bacterial growth can be carried out in vivo, e.g., to inhibit bacterial growth in a living mammal (e.g., a human, or a non-human mammal).

In some embodiments, a subject antimicrobial peptide is contacted with the surface of a medical device in vitro. In some instances, the medical device is an implantable medical device. Implantable medical devices include, but are not limited to, contact lenses, catheters, and the like.

In some instances, a subject anti-microbial peptide provides an antimicrobial effect to a target microbial organism and can be used to treat a disease or infection associated with the target microbial organism. An antimicrobial effect includes inhibiting the growth or killing of the target microbial organisms, or interfering with any biological functions of the target microbial organisms. In general, a subject peptide can be used to treat a disease or infection at any place in a host, e.g., at any tissue including surfaces of any tissue or implant. In one embodiment, the compositions are used to specifically kill or inhibit target microbial organisms in body fluid (e.g., blood, serum, plasma, sputum). In one embodiment, a subject peptide is used to reduce bacterial growth on a surface containing a biofilm.

The term "biofilm" refers to an accumulation of microbial organisms that produce an extracellular polysaccharide and proteinaceous material that act as a natural glue to immobilize or embed the organisms. Biofilms may form on solid biological or non-biological surfaces. A biofilm consisting essentially of non-harmful, non-pathogenic, commensal microbial organisms is essential for maintaining a healthy and normal microbial flora to prevent the invasion and establishment of other pathogenic microbial organisms, e.g., yeast infection. However, if the microorganism population in a biofilm is disturbed by overpopulation of pathogenic microbial organisms, the resulting biofilm may lead to biofilm-associated microbial infection. Examples of biofilm-associated microbial infections include infections of oral soft tissues, teeth and dental implants; middle ear; gastrointestinal tract; urogenital tract; airway/lung tissue; eye; urinary tract prostheses; peritoneal membrane and peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses, internal fixation devices, and percutaneous sutures; and tracheal and ventilator tubing. Indwelling and subcutaneous biomedical implants or devices are potential sites for microbial or biofilm-based infections. Biomedical systems such as blood oxygenators, tracheal lavage, dental water units, and dialyzers are also susceptible to bacterial contamination and biofilm formation.

Where a subject peptide is administered to a mammalian subject, the peptide can be administered in any way which is medically acceptable which may depend on the disease condition being treated. Possible administration routes include parenteral routes such as intravascular, intravenous, ophthalmic, and topical; and pulmonary, e.g., by inhalation. Possible routes of administration include enteral routes, e.g., oral, rectal, etc. The compositions may also be directly applied to tissue surfaces. Sustained release, pH dependent release, or other specific chemical or environmental condition mediated release administration is also specifically included, e.g., by such means as depot injections or erodible implants.

Combination Methods

A subject peptide can be used in a method of reducing bacterial growth alone, or in combination with one or more additional anti-microbial agents, including non-peptide small molecule anti-microbial agents and peptidic anti-microbial agents.

Anti-microbial agents include antibiotics such as penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; chloramphenicol; metronidazole; spectinomycin; trimethoprim; vancomycin; etc.

Anti-microbial peptides include, e.g., alexomycin, andropin, apidaecin, bacteriocin, β-pleated sheet bacteriocin, bactenecin, buforin, cathelicidin, α-helical clavanin, cecropin, dodecapeptide, defensin, β-defensin, α-defensin, gaegurin, histatin, indolicidin, magainin, nisin, protegrin, ranalexin, and tachyplesin.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Keratin-Derived Antimicrobial Peptides

Materials and Methods

Summary

Telomerase-immortalized human corneal epithelial cells (TiHCE) were cultured as described (Robertson D M et al., 2005 *Invest Ophthalmol V is Sci.* 46:470-478). Crude lysates of media-treated and human tear fluid-treated cells were collected by freeze-thawing in KBM or saline (for assays) or 10 mM Tris-HCl (pH 8.5) (for mass spectrometry). Serial fractionation of lysates was performed using centrifugal filters with cutoffs at ~100, ~10 and ~3 kDa (Millipore). Peptides in lysate fractions, including human keratin 6A (hKRT6A) fragments, were detected by standard LC MS/MS with CID and ETD fragmentation, then analyzed with web-based proteomic tools (ExPASy). Expression of hKRT6A by TiHCE cells was confirmed by Western blotting. Lipofectamine RNAi Max (Invitrogen) was used to transfect TiHCE cells with siRNA against hKRT6A (ON-TARGETplus SMARTpool; Dharmacon) or non-targeting scramble control (Dharmacon). SiRNA knockdown efficiency was evaluated by quantitative real-time PCR of hKRT6A (normalized with GAPDH) using QuantiTect SYBR Green PCR Master Mix and Primer Assays (Qiagen). Synthetic peptides of hKRT6A were obtained from Biomatik at a purity of >95%. Antimicrobial activity against *Pseudomonas aeruginosa* clinical and laboratory isolates, as well as ATCC strains of *Escherichia coli, Enterococcus faecalis, Serratia marcescens, Staphylococcus epidermidis, Staphylococcus aureus, Streptococcus pyogenes* and *Candida albicans* ($\sim 10^6$ cfu/ml each) were evaluated by viable counts at 3 h. Protection against bacterial invasion (quantified by gentamicin survival) and cytotoxicity (trypan blue staining) were assessed using fresh TiHCE cells inoculated with *P. aeruginosa* clinical isolates 6294 (invasive, $\sim 10^6$ cfu for 2 h) or 6206 (cytotoxic, $\sim 10^4$ cfu for 3 h). Peptide binding and membrane permeabilization by hKRT6A 19mer was determined by N-terminal TAMRA-tagged peptides (110 µM) and an impermeant SYTOX blue nucleic acid stain (5 µM; Invitrogen). Statistical analysis between two groups was performed using Student's t-Test.

Bacterial Strains

*Pseudomonas aeruginosa* corneal clinical isolates 6294 (invasive) and 6206 (cytotoxic), cystic fibrosis clinical isolate 2192, laboratory strains PAO1 (invasive), PA14 (cytotoxic), PAC1R and its series of isogenic LPS mutants (PAC1R algC-, 557, 605, 611) were used in this study. For antimicrobial spectrum analysis, *Escherichia coli* (ATCC 25922), *Enterococcus faecalis* (ATCC 51188), *Serratia marcescens* (ATCC 43862), *Staphylococcus epidermidis* (ATCC 12228), *Staphylococcus aureus* (ATCC 29213), *Streptococcus pyogenes* (ATCC 19615) and *Candida albicans* (ATCC 90028) were used. *P. aeruginosa* was grown on tryptic soy agar (TSA) plates at 37° C. for 16 h, while other bacteria were grown on nutrient agar plates for 16 h at media and conditions specified by ATCC. Starting inoculum at a concentration of $\sim 10^8$ cfu/ml was prepared fresh by suspending bacteria in KBM media (Lonza) until $OD_{650}$ reading is $\sim 0.1$. Specific bacterial concentration used in antimicrobial and cytoprotective assays was prepared by 10- or 100-fold dilution of this starting inoculum in the indicated test media.

Cell Culture and Lysate Fractionation

Telomerase-immortalized human corneal epithelial (TiHCE) cells (Robertson D M et al., 2005 *Invest Ophthalmol V is Sci.* 46:470-478) were maintained at 37° C./5% $CO_2$ in regular KGM-2 media containing 0.15 mM $CaCl_2$ (Lonza). TiHCE cells in antibiotic-free KGM-2 media were growth to 90% confluence in 96-well tissue culture-treated plates, then switched high-calcium antibiotic-free KGM-2 media (containing 1.15 mM $CaCl_2$) for 16 h, followed by exposure to human tear fluid or high-calcium antibiotic-free KGM-2 media for additional 16 h. Both media-treated and tear-treated cells were then lysed in 25 µl/well of KBM basal media (Lonza) (for antimicrobial and cytoprotective activity assays) or 100 mM Tris-HCl (pH 8.5) (for mass spectrometry) by 3 cycles of freeze and thaw. Crude lysate was pooled and confirmed to have equal total protein concentration. Serial fractionation of crude lysate was performed at 4° C. using sterile water pre-rinsed Microcon centrifugal filter devices with membrane cut-offs at 100, 10 and 3 kDa (Millipore). Fresh vehicle was added back to all lysate fractions to maintain equal volume to their original crude lysates.

SiRNA Transfection and Real-Time PCR

Transfection (6 h) in 96-well plate format was performed when TiHCE cells were 80% confluent using Lipofectamine RNAi Max (Invitrogen) and siRNAs (10 pmol in 100 µl) against human keratin 6A (5'-CGAAGGCGUUGGA-CAAGUC-3' (SEQ ID NO:58); 5'-GAACAAGG-UUGAACUGCAA-3' (SEQ ID NO:59); 5'-GCAGUUCCA-CCAUCAAGUA-3' (SEQ ID NO:60); and 5'-GAGAUCAACUUCCUGAGAG-3' (SEQ ID NO:61); ON-TARGETplus SMARTpool L-012116-00-0005; Dharmacon) or scramble control (ON-TARGETplus Non-targeting Pool D-001810-10-05; Dharmacon), followed by 16 h of recovery in antibiotic-free KGM-2, then 16 h of differentiation in high-calcium antibiotic-free KGM-2 (containing 1.15 mM $CaCl_2$). To collect lysate for antimicrobial assays, cells were lysed in 25 µl/well of saline (0.9% NaCl) by 3 cycles of freeze and thaw, and crude lysate was pooled and confirmed to have equal total protein concentration prior to use. To confirm successful knockdown, total RNA was isolated using RNeasy Mini Kit (Qiagen), and 1 µg was used for cDNA synthesis using Verso cDNA Synthesis Kit (Dharmacon). Keratin 6A and GAPDH (internal control) were amplified from cDNA (0.5 µL of each cDNA sample per 10 µL of PCR reaction) using QuantiTect SYBR Green PCR Master Mix and Primer Assays (Qiagen). Samples were analyzed in triplicates in three independent runs using a real-time detection system (Bio-Rad). Transcript levels of keratin 6A were normalized to that of GAPDH.

Peptide Synthesis

All peptides (with or without n-terminal TAMRA-tag) were synthesized by Biomatik to >95% purity and verified by HPLC and MS. Stock solutions were prepared in sterile water, and aliquots were kept at $-20°$ C. and limited to one thaw prior to use.

Mass Spectrometry

Mass spectrometry was performed by the Proteomics/Mass Spectrometry Laboratory at UC Berkeley. A nano LC column was packed in a 100 µm inner diameter glass capillary with an emitter tip. The column consisted of 10 cm of Polaris c18 5 µm packing material (Varian). The column was loaded by use of a pressure bomb and washed extensively with buffer A (see below). The column was then directly coupled to an electrospray ionization source mounted on a Thermo-Fisher LTQ XL linear ion trap mass spectrometer. An Agilent 1200 HPLC equipped with a split line so as to deliver a flow rate of 30 nl/min was used for chromatography. Peptides were eluted with a 90 minute gradient from 100% buffer A to 60% buffer B. Buffer A was 5% acetonitrile/0.02% heptaflurobutyric acid (HBFA); buffer B was 80% acetonitrile/0.02% HBFA. CID and ETD spectra were collected for each M/Z. The programs SEQUEST and DTASELECT were used to identify peptides and proteins from the human database (Eng J K et al., 1994 *J. Am. Soc. Mass Spectrom.* 5:976-989; Tabb D L et al., 2002 *J Proteome Res.* 1:21-26).

Bioinformatics

Peptide sequences were analyzed using web-based tools hosted on the ExPASy (Expert Protein Analysis System) proteomics server of the Swiss Institute of Bioinformatics (<http://>followed by <ca(dot)expasy(dot)org/tools/#proteome>). Specifically, ProtParam was used to compute theoretical pI, NetSurfP for secondary structure prediction, TMpred for transmembrane helices prediction, HeliQuest for amphipathicity and net charge computation as well as helical wheel presentations.

Western Blotting

Detection of human keratin 6A and GADPH proteins in crude lysate of media-treated and tear-treated TiHCE cells (containing 10 μg of total protein) were performed by standard Western blotting using rabbit monoclonal anti-cytokeratin 6 antibody (clone EPR1603Y; Origene) and rabbit polyclonal anti-GAPDH antibody (sc-25778; Santa Cruz) respectively, followed by goat anti-rabbit IgG-HRP secondary antibody (Bio-Rad).

Antimicrobial Activity Assay

Bacteria (60 μl; $10^6$ cfu/ml) in whole lysate, lysate fractions, and saline with indicated peptides as well as the corresponding vehicle controls were incubated in triplicates at 37° C. for 3 h. Serial dilutions of the samples at time 0 and 3 h were plated on nutrient agar plates and incubated at 37° C. overnight for viable bacterial counts (cfu/ml). Percent of bacterial killing at 3 h was expressed as (bacterial counts without peptide−bacterial counts with peptide)/bacterial counts without peptide×100%.

Invasion and Cytotoxicity Assay

To assess protective activity of against bacterial invasion, high-calcium treated TiHCE cells were incubated with P. aeruginosa clinical isolate 6294 (40 μl/well; $10^6$ cfu/ml in crude lysates/lysate fractions versus KBM control for 3 h or $10^8$ cfu/ml in peptide-containing saline versus no-peptide saline control for 2 h), followed by gentamicin treatment (200 μg/ml for 1 h). Viable intracellular bacteria was collected with 0.25% Triton-X in PBS (100 μl/well) and quantified by plating on TSA. To assay protection against bacterial cytotoxicity, P. aeruginosa clinical isolate 6206 was used instead (40 μl/well; $10^6$ cfu/ml for 3 h). Dead cells were quantified by Trypan-blue (0.04%) staining.

Phase Contrast and Fluorescence Microscopy

To assess bacterial motility, P. aeruginosa clinical isolate 6206 (200 μl; $10^6$ cfu/ml in saline) were incubated with or without peptide (200 ug/ml synthetic 19mer peptide or its scrambled control peptide) at 37° C. for 3 h. Aliquots (3 μl each) of the mixtures were immediately placed on precleaned microscope slides, and real-time bacterial motility was visualized with an Olympus IX70 epifluoresence microscope equipped with a 63× objective and phase contrast. To assess peptide binding and membrane permeabilization, bacteria (200 μl; $10^6$ cfu/ml in saline) were incubated at 37° C. for 2.5 h with or without indicated peptides including TAMRA-tag peptides and TAMRA tag control (Invitrogen) at equimolar concentration of 110 μM, followed by 30 min incubation with the impermeant SYTOX blue nucleic acid stain (5 μM; Invitrogen). Bacteria were pelleted by centrifugation and supernatant was removed before resuspension in 10 μl of saline. Bacteria were visualized by phase contrast, SYTOX blue and TAMRA fluorescence under a 100× objective.

Statistical Analysis

Data were expressed as mean±standard deviation (SD). Statistical significance between two groups was determined by Student's t-Test. P values of <0.05 were considered significant.

Results

Figure 1B:
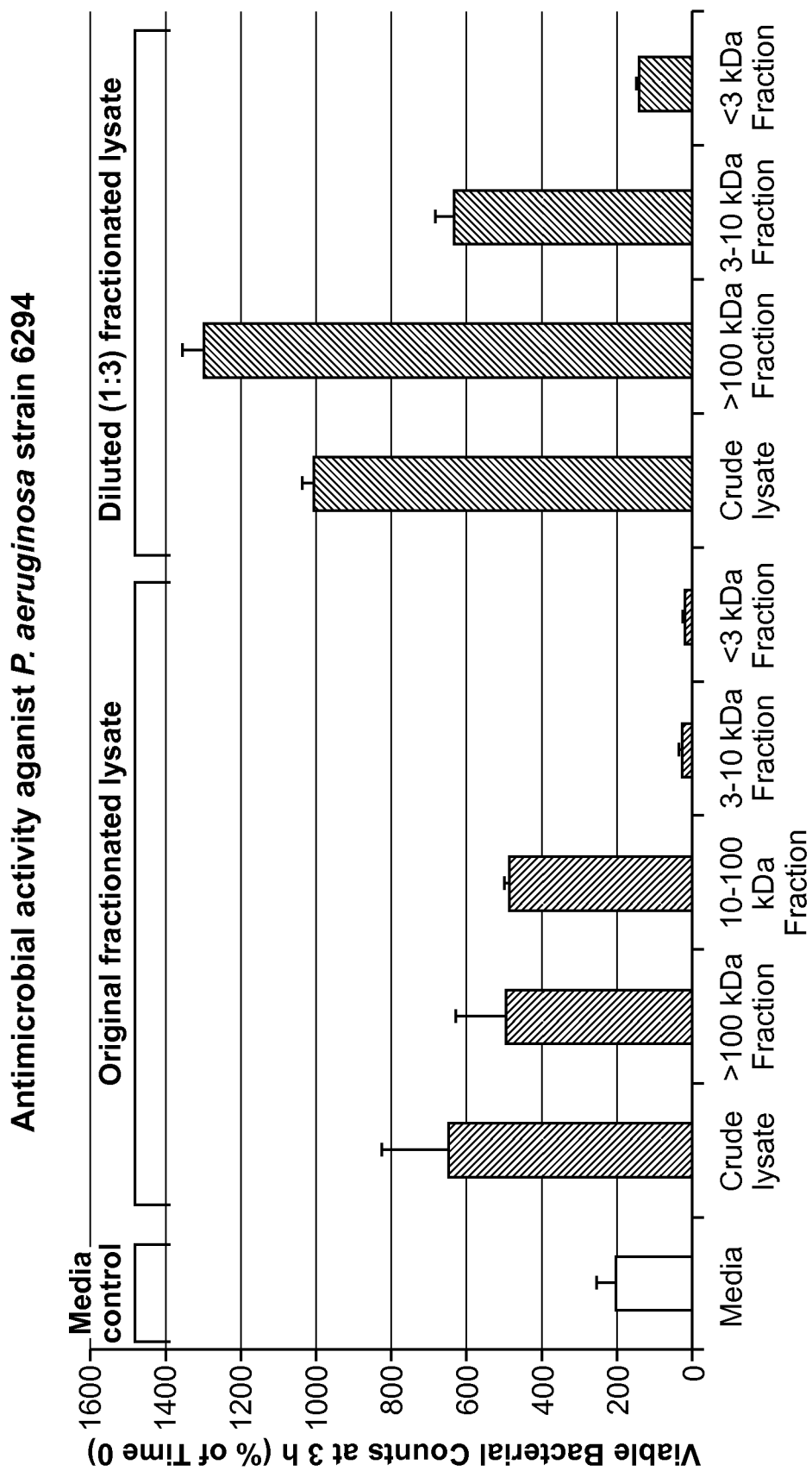
Figure 1C:
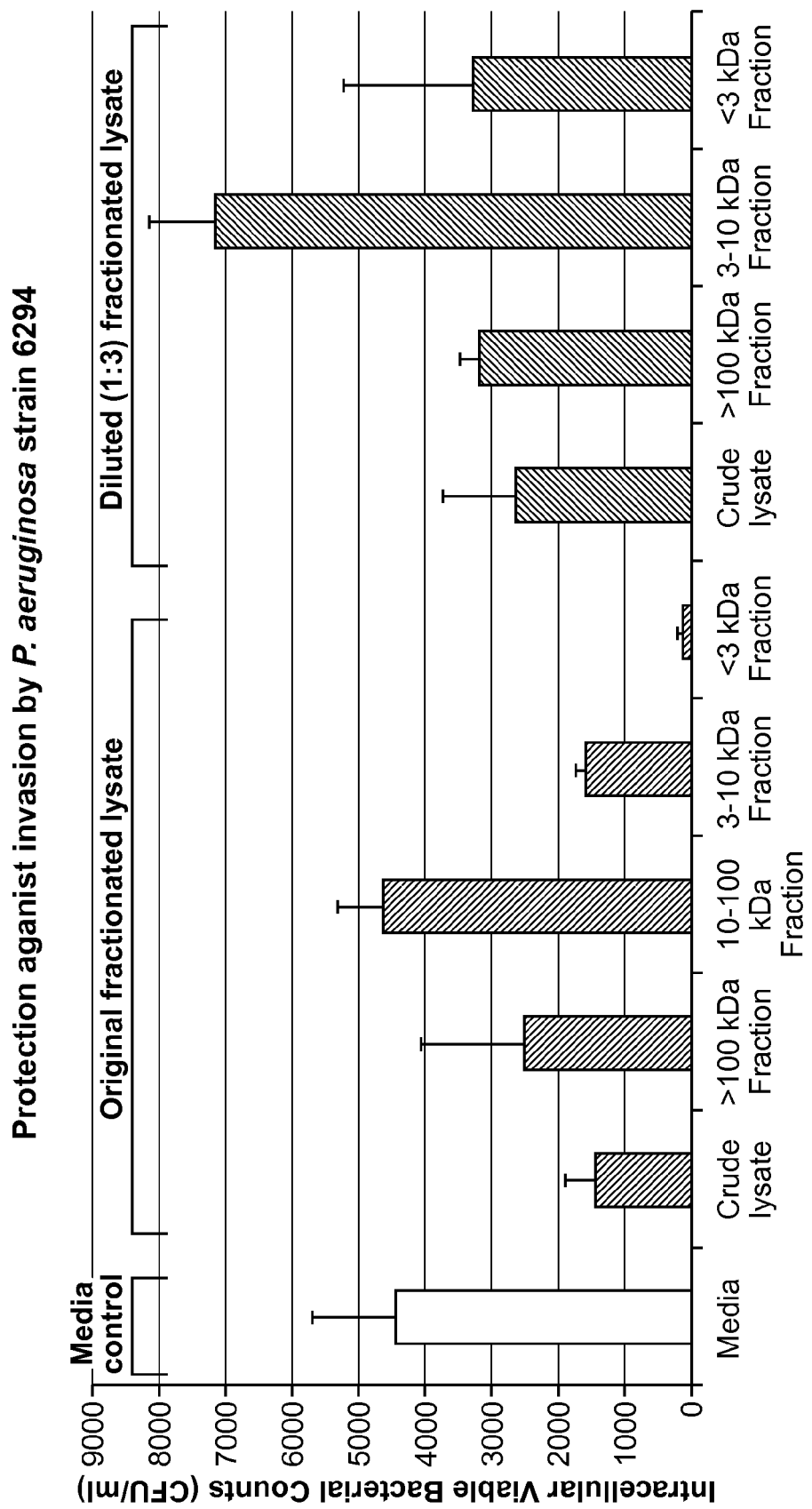
Figure 1D:
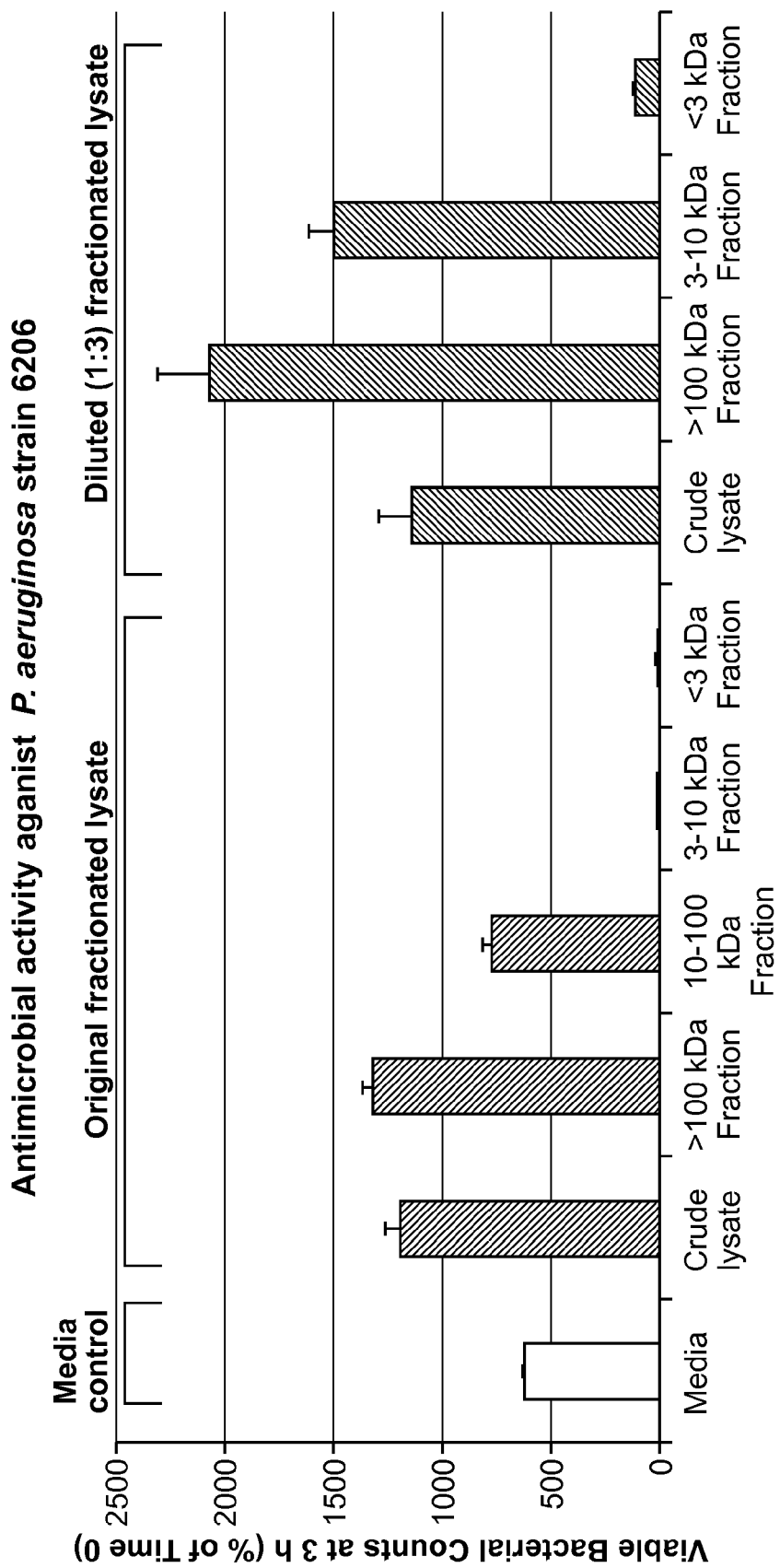

Cultured human corneal epithelial cells were lysed and fractionated, and fractions screened for bactericidal activity against P. aeruginosa strains PAC1R (a lab isolate), clinical isolate 6206 (cytotoxic) and clinical isolate 6294 (invasive). For PAC1R the results revealed that lysate fractions containing small molecules (<3 kDa) were the most effective in killing bacteria (FIG. 1A). For 6206 and 6294, both the <3 kDa and the 3-10 kDa lysates were bactericidal and this was found concentration dependent (FIG. 1B, FIG. 1D).

Figure 1E:
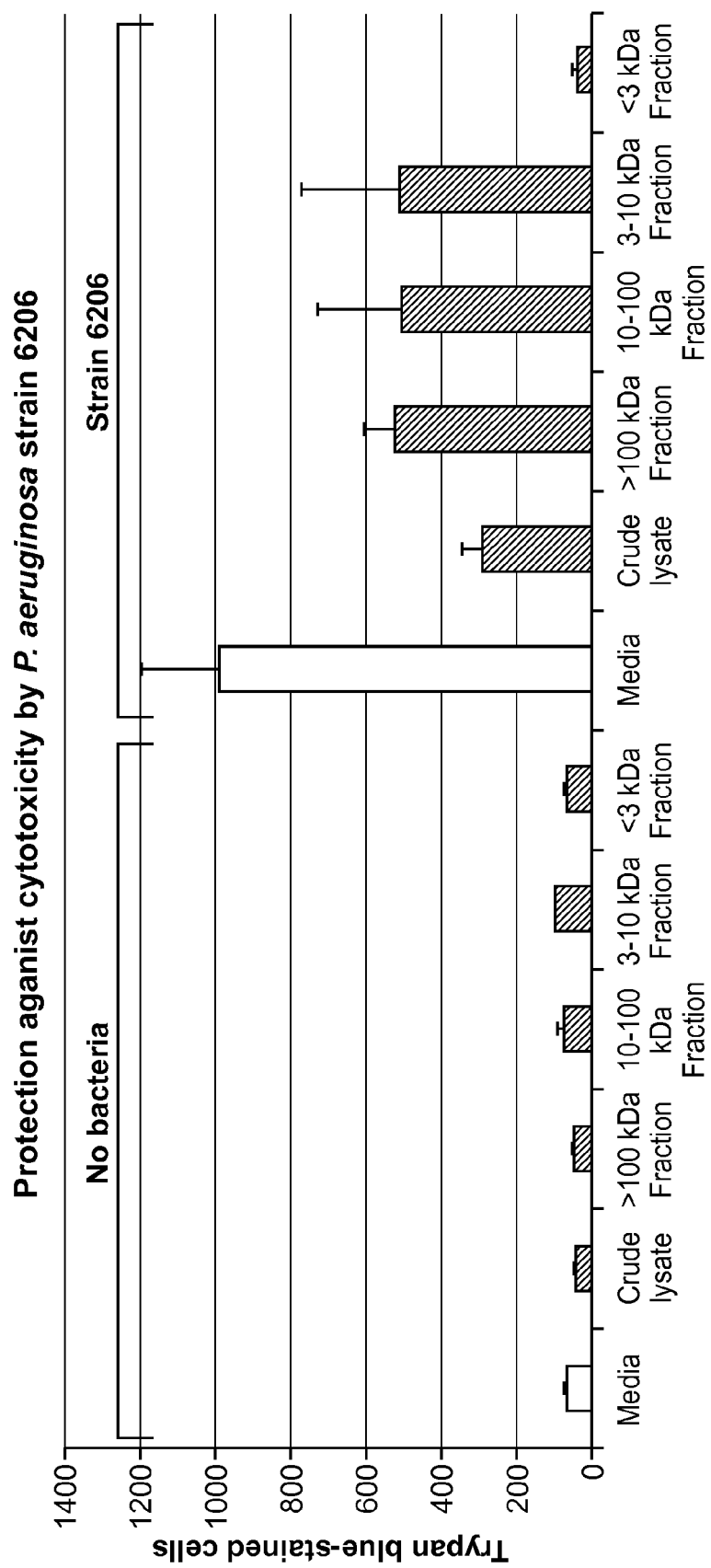

To examine functional significance of antimicrobial activity in epithelial cell lysates, the antimicrobial lysate fractions were next tested for capacity to modulate invasion of human corneal epithelial cells by P. aeruginosa. Both the <3 and the 3-10 kDa small molecule lysate fractions protected live human corneal epithelial cells against P. aeruginosa invasion in vitro, which was again concentration-dependent (FIG. 1C). Additionally, the <3 kDa fraction was able to protect cells against the normal cytotoxic activity associated with P. aeruginosa strain 6206 (FIG. 1E).

Figure 1F:
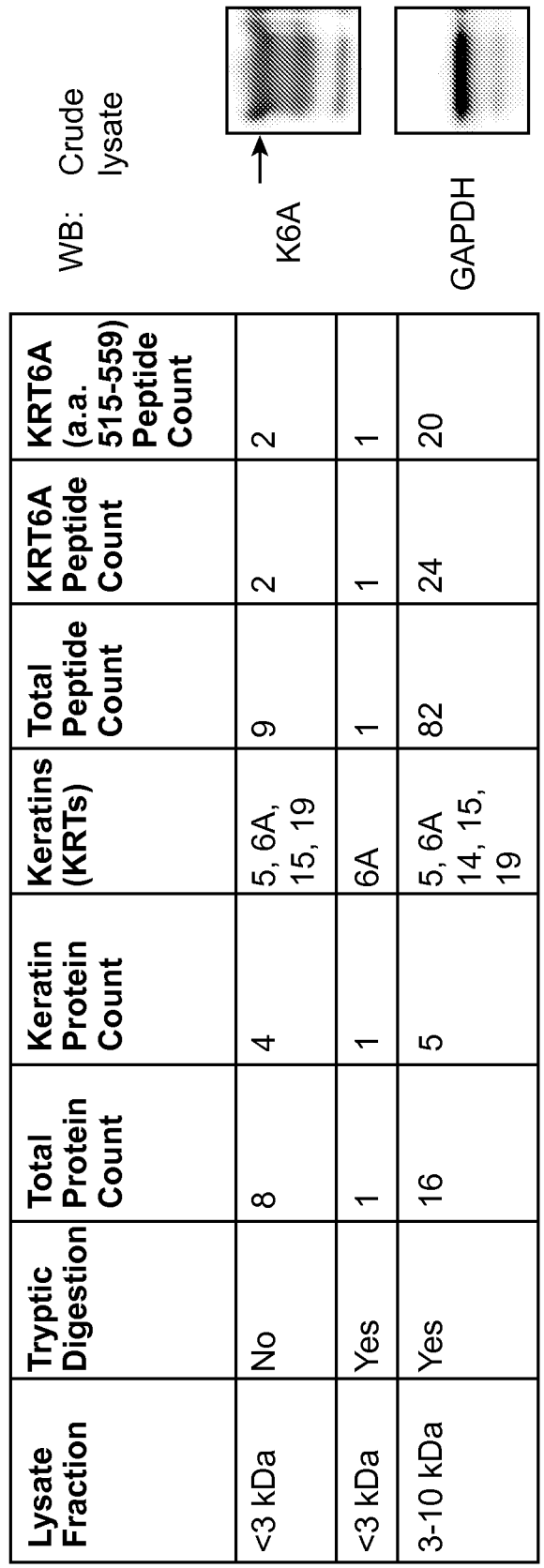

Since known antimicrobial peptides tend to be in the ~3-10 kDa or larger size range (Zasloff M, 2002 Nature. 415:389-395), the presence of bactericidal and cytoprotective activity in the <3 kDa fraction suggested novel antimicrobials might be contained within. Thus, lysate fractions were analyzed for their peptide content using LC MS/MS mass spectrometry (FIG. 1F, left panel). To identify native peptides in the <3 kDa fraction, non-trypsin digested fractions were initially analyzed. A 17-amino-acid peptide fragment (AIGGGLSS-VGGGSSTIK; SEQ ID NO:1) from the human cytoskeletal protein keratin 6A (hKRT6A, a.a. 534-550), was consistently detected in these fractions with or without trypsin processing. Interestingly, both the N- and C-terminal amino acids of this fragment (Ala and Lys, respectively) were flanked by a theoretical trypsin cleavage site (Arg-Ala and Lys-Tyr, respectively), suggesting this fragment could be proteolytically released from full-length keratin 6A, e.g. via endogenous trypsin or trypsin-like serine proteases. Tryptic digestion of the 3-10 kDa fraction consistently revealed the same 17mer fragment, and a series of overlapping peptides comprising the full or partial sequence (variants) (FIG. 1G). These peptides and peptide fragments belonged to the C-terminal region (a.a 515-559) of hKRT6A. Western immunoblot confirmed the presence of KRT6A in crude corneal epithelial cell lysates (FIG. 1F, right panel).

Figure 2A:
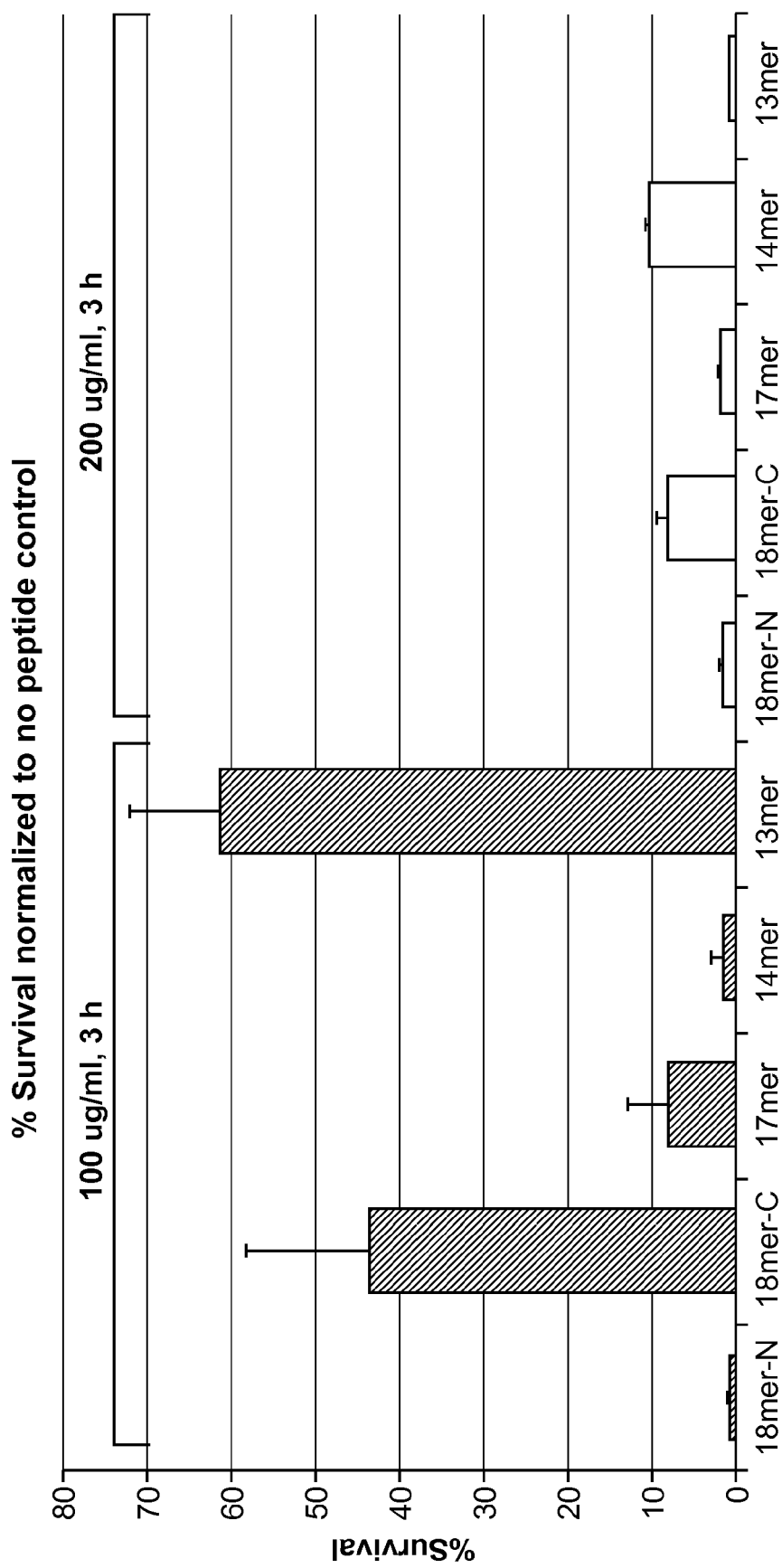
FIG. 2A-2G depict activity of synthetic analogs of keratin 6A-derived peptides.

The potential of keratin 6A fragments to function as antimicrobial peptides was explored using ExPASy proteomic tools which can predict peptide secondary structures, transmembrane helices, amphipathicity and net charges (Leptihn S et al., 2010 Biochemistry. 49:9161-9170; Gautier R et al., 2008 Bioinformatics. 24:2101-2102; Petersen B et al., 2009 BMC Struct Biol. 9:51; Hofmann K and Stoffel W, 1993 Biol. Chem. Hoppe-Seyler. 374) (FIG. 1G, FIG. 1H). At least two 18-amino-acid fragments (variants of the 17mer fragment with an additional N- or C-terminal residue) were predicted favorable for antimicrobial activity. Given this, and the fact that a significant proportion of the identified peptides in the antimicrobial fractions were keratin fragments, that keratin 6A-derived peptide fragments were present in all antimicrobial fractions, and in some instances it was the only peptide identified, we decided to pursue them as candidates for antimicrobial activity. Synthetic versions of the 17mer peptide and other variants detected in the corneal cell lysate (i.e. 18mer-N, 18mer-C, 14mer and 13mer) were tested against P. aeruginosa strain 6206. Each of these peptides (at 200 μg/ml) showed bactericidal activity (>90% killing) comparable to that of the 17mer peptide (FIG. 2A). At 100 μg/ml, bacterial killing by the 18mer-N, 18mer-C, 17mer, 14mer and 13mer was 99.4%, 56.5%, 92.3%, 98.8%, 38.1% respectively (P<0.01), and 98.5%, 91.9%, 98.3%, 89.8%, 99.4% at 200 μg/ml (P<0.0005).

FIG. 1A-1H: Detection of keratin 6A-derived peptides in <3 kDa and 3-10 kDa antimicrobial fractions of human corneal epithelial cell lysates. (FIG. 1A) Crude lysates were serially fractionated by size to yield four fractions: >100 kDa, 10-100 kDa, 3-10 kDa and <3 kDa (purple). Crude lysates, and the small molecule <3 kDa lysate fraction were bactericidal against *P. aeruginosa* (strain PAC1R). Culture media was fractionated in parallel to serve as controls for the corresponding lysate fractions in the bacterial killing assays (green). (FIG. 1B) Similar results were observed for *P. aeruginosa* clinical isolate 6294, except that 3-10 kDa lysate fractions were also found to be bactericidal. Dilution (1:3) (light purple) reduced activity, demonstrating antimicrobial activity was concentration-dependent. (FIG. 1C) <3 kDa and 3-10 kDa fractions both protected epithelial cells against *P. aeruginosa* internalization. (FIG. 1D) <3 kDa fraction was bactericidal against a cytotoxic *P. aeruginosa* clinical isolate (strain 6206) and, (FIG. 1E) protected epithelia from bacterial-induced cell death (indicated by trypan blue-staining). (FIG. 1F) (left) mass-spectrometric analysis of <3 kDa and 3-10 kDa lysate fractions revealed multiple keratin-derived peptide fragments with keratin 6A common to all samples. (FIG. 1F) (right) Western blot confirmed expression of keratin 6A by corneal epithelial cells. (FIG. 1G-1H) Sequence, predicted structural characteristics, and helical wheel representations of keratin 6A-derived peptides found in <3 kDa and 3-10 kDa lysate fractions (i.e. 18mer-N, a.a. 534-551; 18mer-C, a.a. 533-550; 17mer, a.a. 534-550; 14mer, a.a. 537-550; 13mer, a.a. 534-546).

Figure 2B:
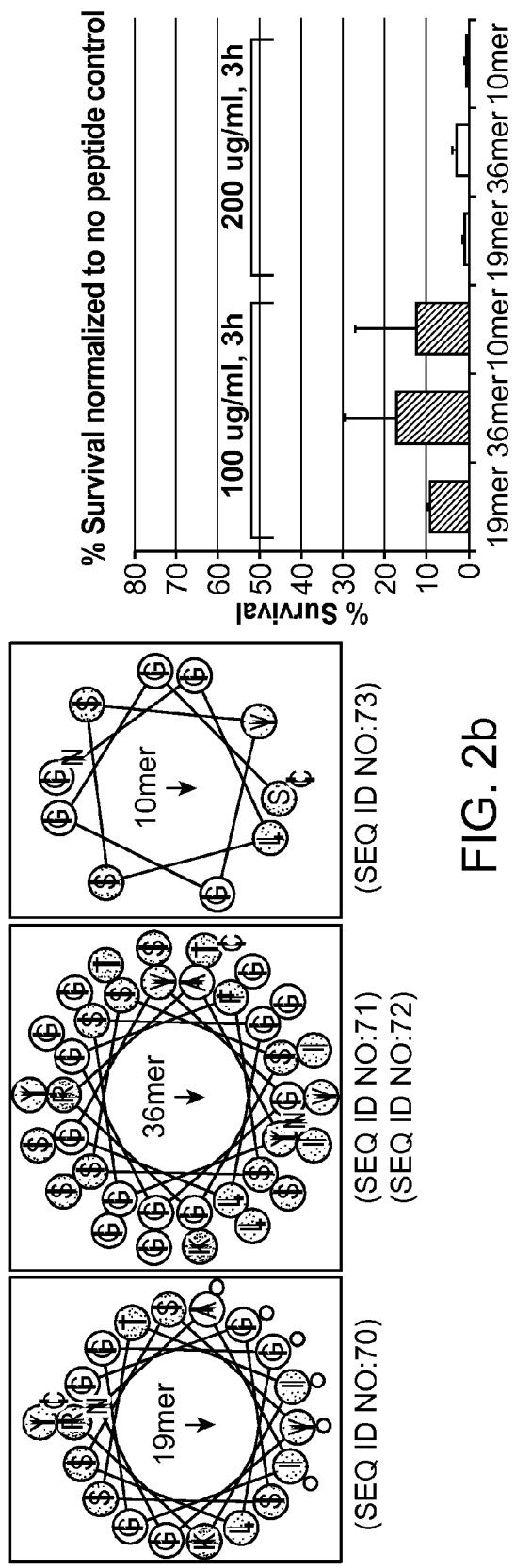

While this result was surprising as peptides with less favorable predicted features for antimicrobial function (e.g. less positive charge, lower hydrophobic moment, or lack of a hydrophobic face etc.) could still be effective, other examples exist of antimicrobial peptide derivatives retaining activity, including some defensins (Reynolds N L et al., 2010 *Antimicrob Agents Chemother.* 54:1922-1929). We thus examined variants of the 17mer with longer or shorter peptide sequence. A 19-amino-acid variant of the KRT6A 17mer (a.a. 533-551) was predicted to have characteristic features of classical cationic antimicrobial peptides based upon +2 positive charge at pH 7.0, hydrophobicity moment of 0.279 pH, and coil structure with transmembrane helices, while a long variant (36mer) and a short variant (10mer) were predicted to be less favorable (FIG. 2B, left panel). Interestingly, each of these peptides (at 200 µg/ml), including the 10-amino-acid fragment, retained bactericidal activity comparable to that of the 17mer peptide (FIG. 2B, right panel). At 100 µg/ml, killing of *P. aeruginosa* strain 6206 by the 19mer, 36mer and 10mer was 90.8%, 83.0%, 87.7% respectively (P<0.0005), which increased to 99.1%, 96.9%, 99.2% at 200 µg/ml (P<0.0005).

Figure 2C:
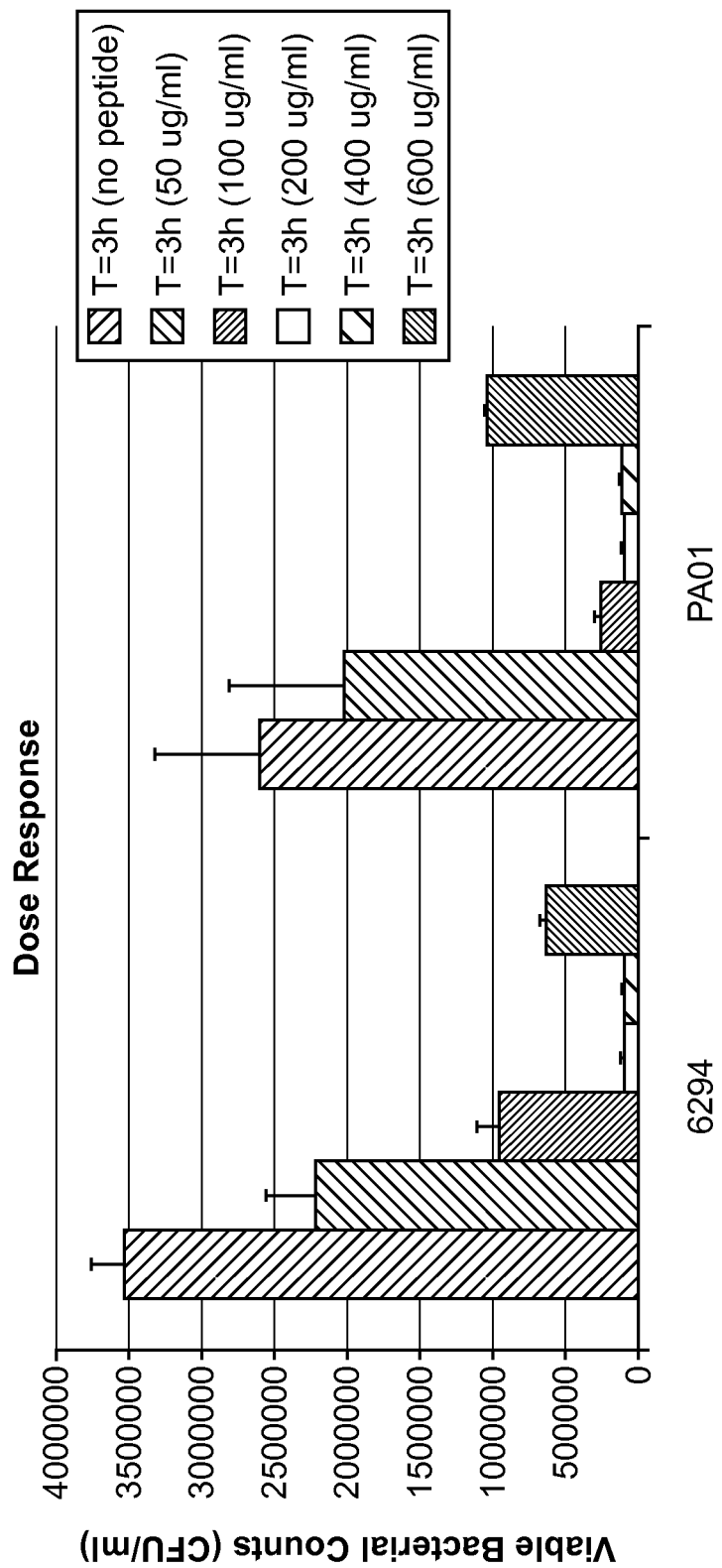
Figure 2D:
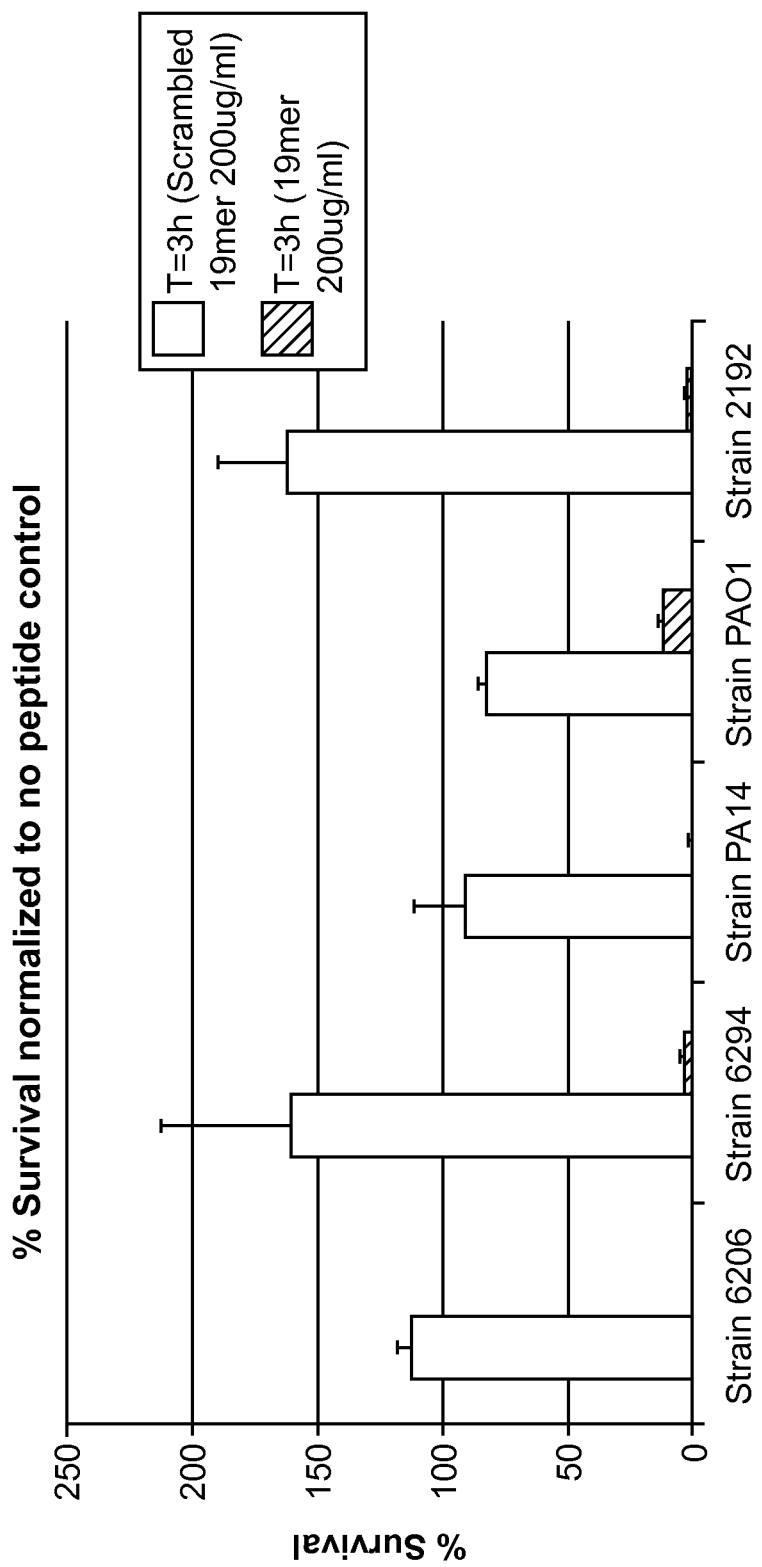
Figure 2E:
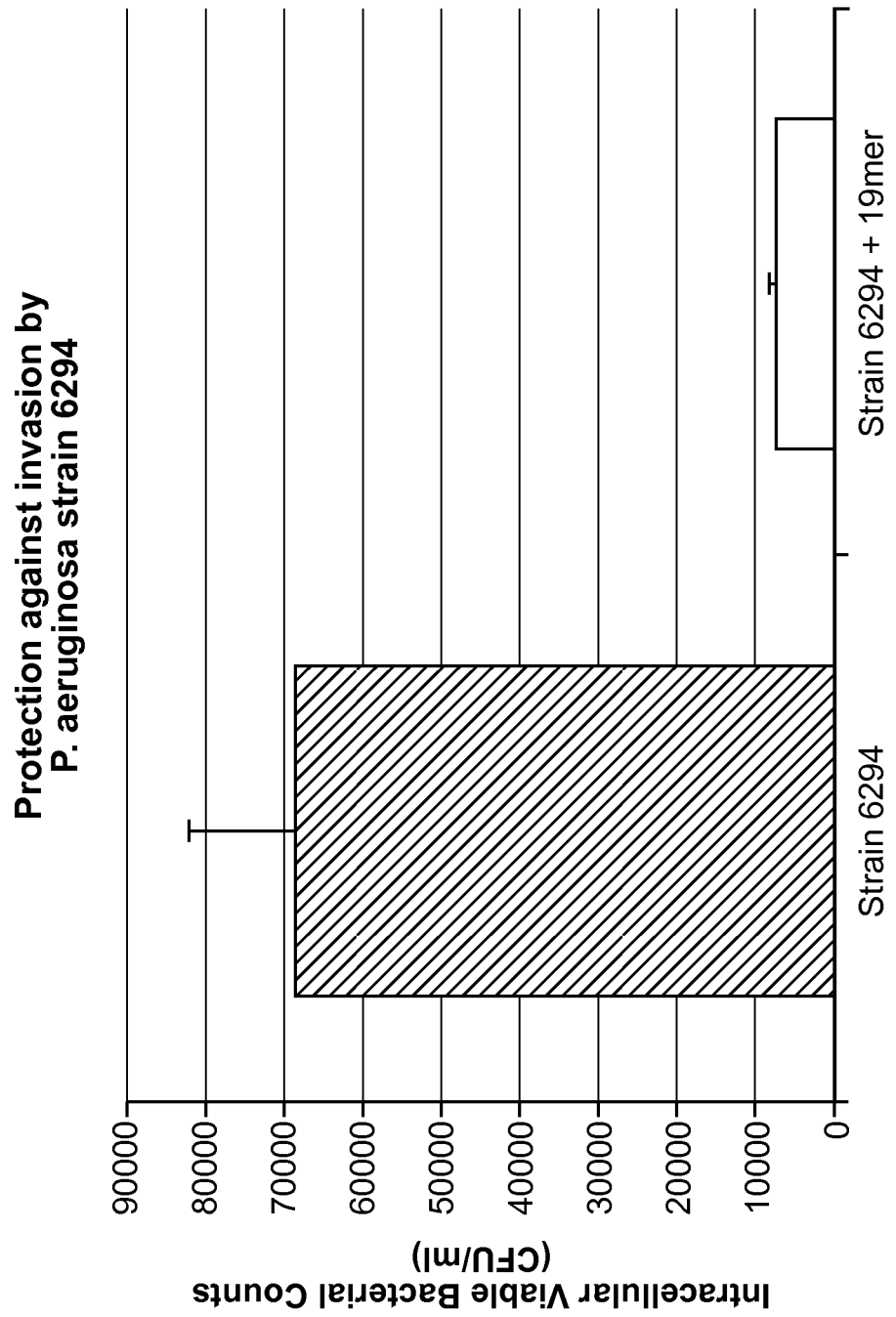
Figure 2F:
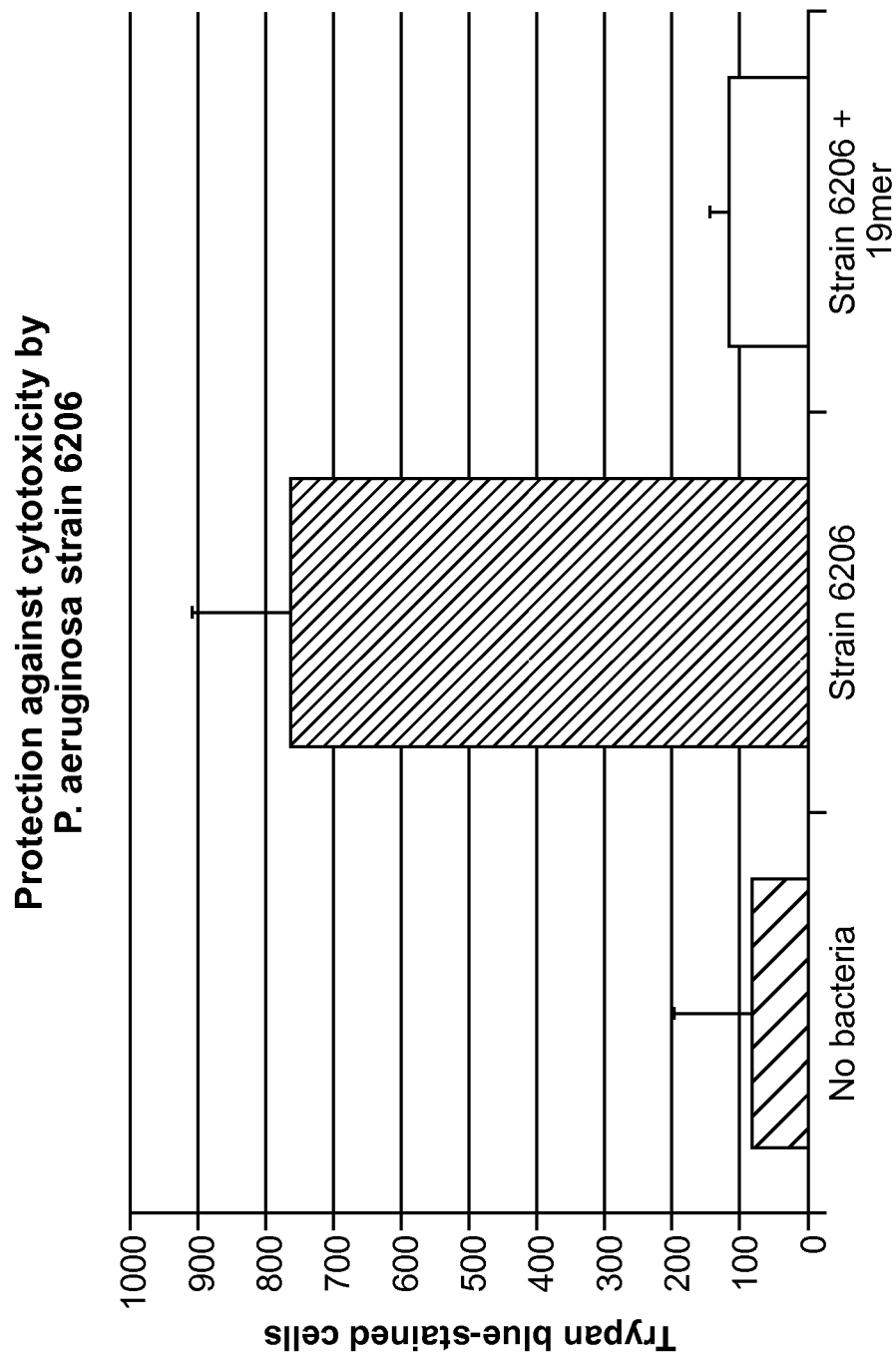

Thus, the antimicrobial activity of the 19mer was further characterized in a dose-response study against clinical isolate 6294 (97.5% reduced viability after 3 h, 200 µg/ml in 0.9% NaCl) and laboratory strain PAO1 (96.1% reduction, same conditions) (P<0.005) (FIG. 2C). A scrambled control of the 19mer peptide was not bactericidal (FIG. 2D) confirming sequence specificity of the antimicrobial activity against 6294, PAO1, and three other *P. aeruginosa* isolates: the cytotoxic isolate 6206, laboratory strain PA14, and cystic fibrosis isolate 2192 (reduced viability by 99.7%, 98.7% and 96.9% respectively) (P<0.01) (FIG. 2D). Peptide-treated bacteria lost capacity for swimming motility as observed using real-time phase-contrast microscopy, visually demonstrating loss of bacterial viability.

Consistent with its bactericidal activity against *P. aeruginosa*, treatment of cultured epithelial cells with the 19mer peptide during bacterial challenge protected them against bacterial invasion and bacterial induced cytotoxicity as compared to controls (by 89.1% and 85.1% respectively; P<0.001). The epithelial cells themselves were not visibly impacted by peptide treatment alone, as revealed by their normal morphology and exclusion of trypan blue.

Figure 2G:
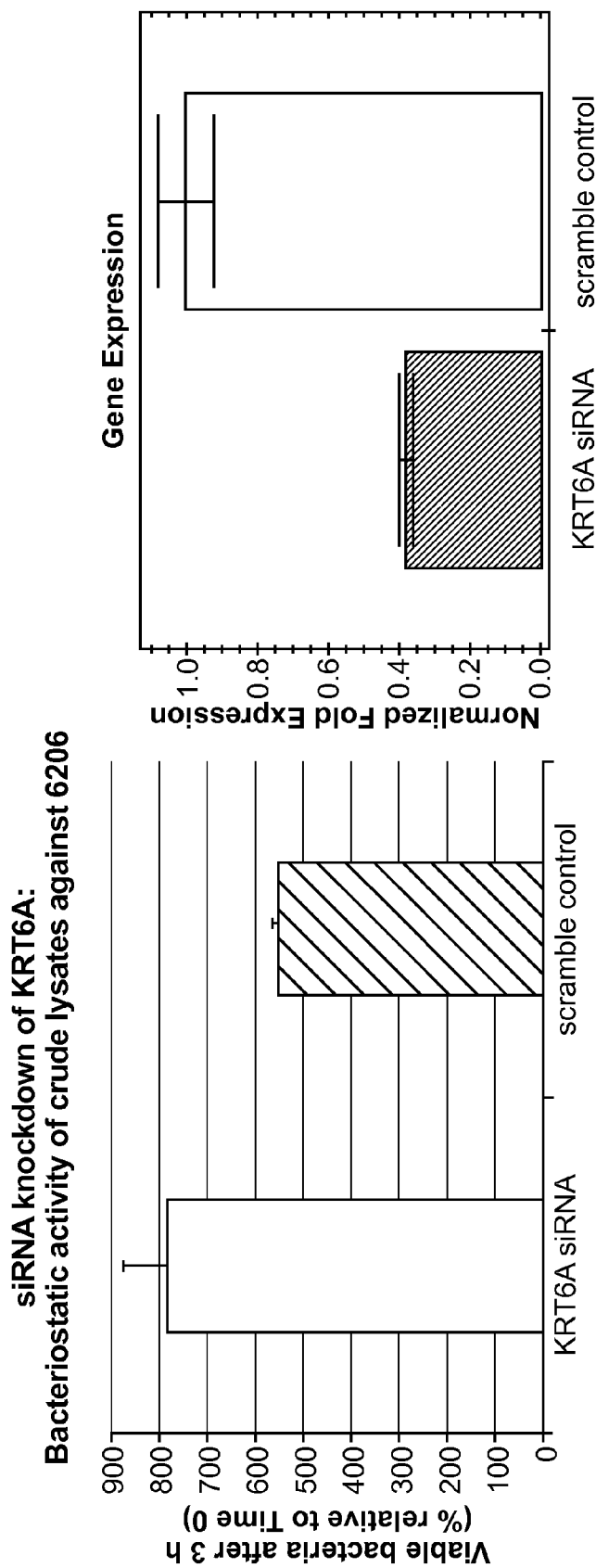

Since the data showed that a 19mer synthetic peptide based upon a fragment of keratin 6A has antimicrobial activity against *P. aeruginosa* and can be used to protect cells against *P. aeruginosa* virulence mechanisms without associated toxicity, we next directly explored if endogenously expressed keratin 6A contributes to the antimicrobial activity of cell lysates, using siRNA to knockdown its expression. Results confirmed keratin 6A knockdown, and that knockdown significantly reduced bacteriostatic activity in cell lysates compared to cells treated with control scrambled siRNA (FIG. 2G). Knockdown also had no significant impact on cell density, morphology or viability as demonstrated by trypan blue exclusion. Together, these data demonstrate the existence of keratin derived antimicrobial peptides (KDAMPs).

FIG. 2A-2G: Synthetic analogs of keratin 6A-derived peptides found in corneal epithelial cell lysates had bactericidal and cytoprotective activity against *P. aeruginosa*; accordingly siRNA knockdown of keratin 6A in corneal epithelial cells reduced the antimicrobial activity of their lysates. (FIG. 2A) Synthetic analogs of keratin 6A-derived peptides found in epithelial cell lysate (18mers, 17mer, 14mer and 13mer) showed dose-dependent bactericidal activity against *P. aeruginosa* strain 6206 (clinical isolate). (FIG. 2B) (left) A 19-amino-acid peptide (a.a. 533-551) encompassing all five fragments (shown in FIG. 2A) was predicted to be a cationic peptide. A 36-amino-acid variant representing a combined sequence of two detected fragments (a.a. 517-533 and a.a. 534-552) parted by a tryptic cut site, and a 10-amino-acid variant representing the overlapping region between 14mer and 13mer were also assessed. (FIG. 2B) (right) Synthetic variants of the 19mer peptide as small as 10 amino acids retained bactericidal activity against *P. aeruginosa* (strain 6206) at 200 µg/mL, despite a predicted loss of cationic charge (at pH 7.0), hydrophobic face, and ability to form a transmembrane helix for the 10mer variant. (FIG. 2C) The 19mer peptide showed dose-dependent bactericidal activity against *P. aeruginosa* strains 6294 (clinical isolate) and PAO1 (laboratory strain) with optimal activity at 200 µg/ml. (FIG. 2D) At 200 µg/ml, a scrambled control of the 19mer peptide was inactive against various strains of *P. aeruginosa*. (FIG. 2E) Invasion of epithelial cells (by invasive strain 6294), and (FIG. 2F) cytotoxicity towards epithelial cells (by cytotoxic strain 6206), were each prevented by the 19mer keratin 6A-derived peptide. (FIG. 2G) (left) Antimicrobial activity of crude epithelial cell lysate was attenuated by siRNA knockdown of keratin 6A. (FIG. 2G) (right) Knockdown efficiency was confirmed by qRT-PCR.

Figure 3B:
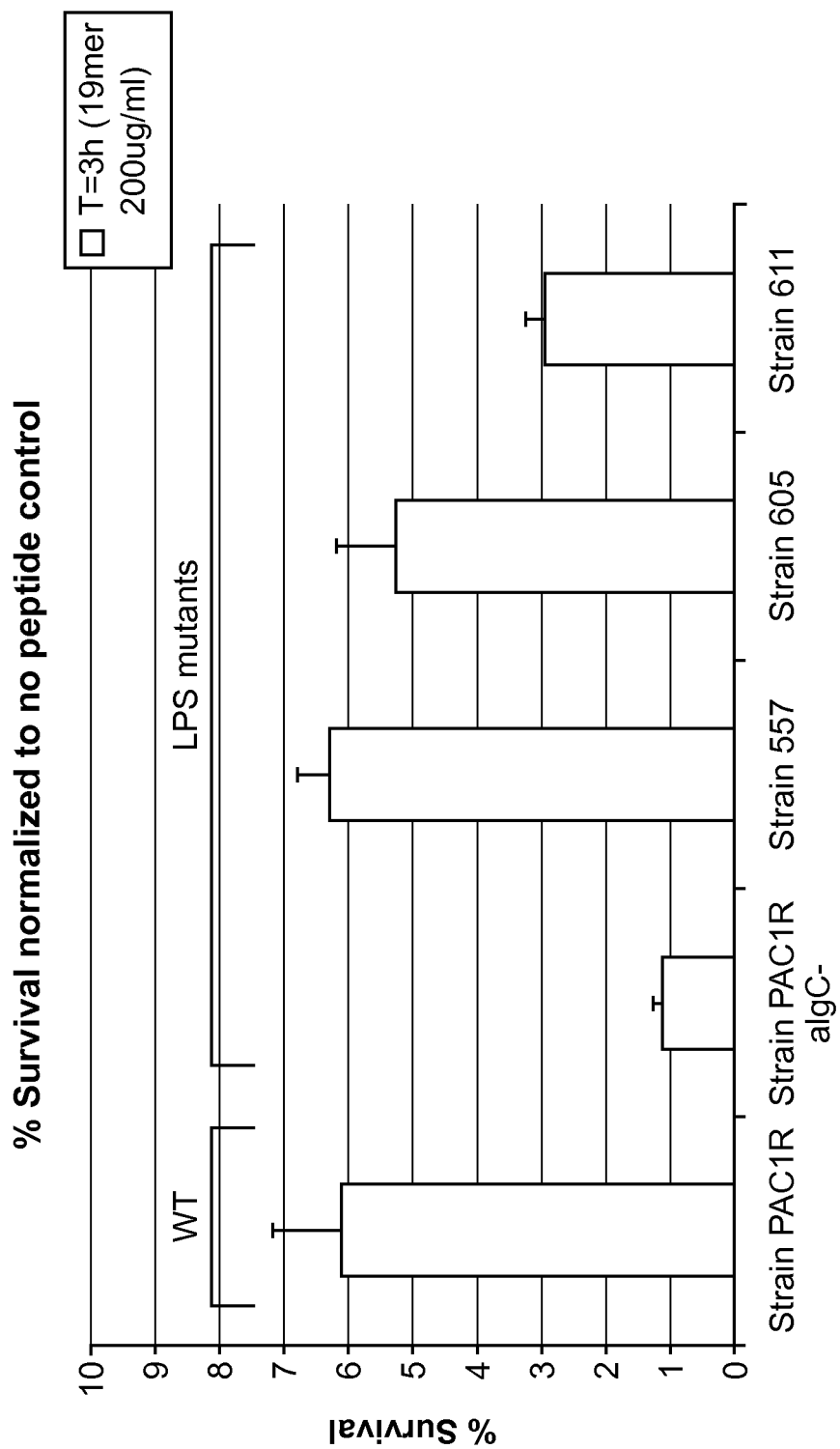

To begin to elucidate how KDAMPs kill bacteria, *P. aeruginosa* strain 6206 was treated with the 19mer peptide tagged with a fluorochrome (TAMRA), and bacteria were stained with SYTOX Blue, a cell-impermeant dye. Fluorescence microscopy revealed that peptide-treated bacteria were TAMRA-labeled (red), immobile, and co-labeled with SYTOX (blue) (FIG. 3A, left panel). Untreated control bacteria did not label with SYTOX, showing that their membranes remained impermeable to the dye (data not shown). Bactericidal assays (FIG. 3A, right panel) confirmed antimicrobial activity of TAMRA-tagged 19mer, and no activity for TAMRA used alone. These results suggested that the 19mer derivative of KRT6A binds bacterial cells and that it permeabilizes the bacterial membrane. Permeabilization could involve direct pore formation by the peptide, as shown for other cationic antimicrobial peptides (Yeaman M R and Yount N Y, 2003 *Pharmacol Rev.* 55:27-55), or permeabilization might be secondary to peptide-induced cell death via another mechanism such as inhibition of other cellular functions. The latter could be possible considering killing was independent of cationic state for some fragment derivatives. Supporting this, mutations in *P. aeruginosa* lipopolysaccharide (LPS), a cell wall molecule of Gram-negative bacteria that hinders cationic antimicrobial peptide activity, had only a small impact on susceptibility to the 19mer KRT6A derivatives, as shown by comparison of wild-type *P. aeruginosa* strain PAC1R with various LPS-defective mutants (Coyne M J et al., 1994 *J. Bacteriol.* 176:3500-3507) (FIG. 3B). Further studies will be needed to define the relationship between 19mer-induced bacterial cell death and bacterial permeabilization.

FIG. 3A and FIG. 3B: The keratin 6A-derived 19mer binds to bacterial cells and results in permeabilization of their membranes. (FIG. 3A) (left) *P. aeruginosa* strain 6206 was treated with TAMRA-tagged (N-terminal) 19mer (250 µg/mL, 110 µM) for 3 h then stained with an cell-impermeant dye SYTOX Blue. Fluorescence microscopy showed that the bacteria labeled with the TAMRA-tagged 19mer peptide (red) and SYTOX (blue) and that these labels colocalize. (FIG. 3A) (right) TAMRA-tagged 19mer had similar bactericidal activity to unlabeled peptide (93.2% and 98.4% respectively, $P<0.05$) after 3 h at 110 µM against *P. aeruginosa* (strain 6206). TAMRA alone was inactive. (FIG. 3B) Bactericidal activity of unlabeled 19mer (200 µg/mL) was only slightly affected by mutations in bacterial LPS for *P. aeruginosa* (strain PAC1R, serigraph 03). PAC1RalgC- and PAC605 have an incomplete LPS core oligosaccharide and are O antigen deficient (Coyne M J et al., 1994 *J. Bacteriol.* 176:3500-3507), PAC557 has a complete core, but is O antigen deficient, while PAC611 has mutations only in the core (Rowe P S and Meadow P M, 1983 *Eur J. Biochem.* 132:329-337).

Figure 4A:
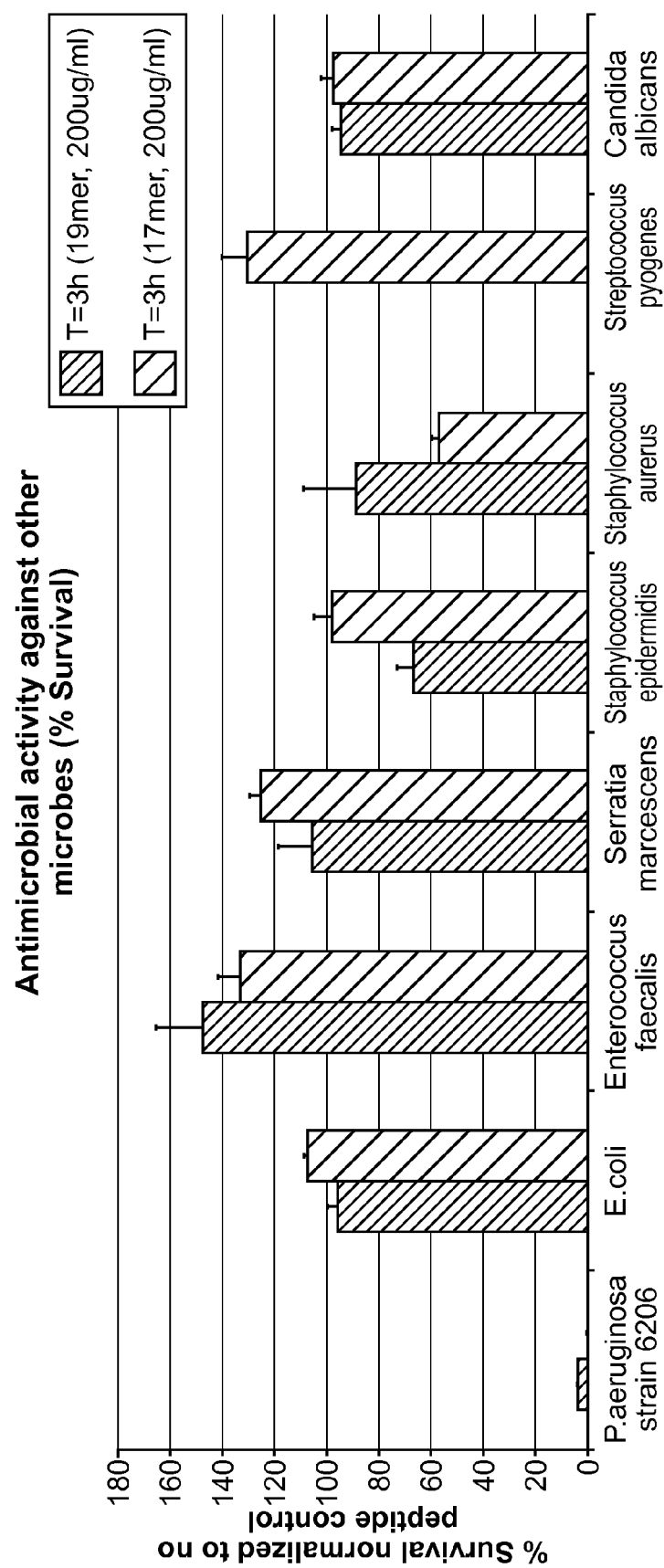
FIG. 4A-4B depict activities of keratin 6A-derived 19-mer.

We next explored spectrum of activity against other microbes. To do that, bactericidal activity of the 19mer and 17mer peptides was examined for a panel of clinically important bacteria and yeast (FIG. 4A). Among them, only *Steptococcus pyogenes* (Group A *Streptococcus*) was found sensitive to the 19mer KRT6A-derivative (99.96% killing after 3 h at 200 µg/ml) ($P<0.001$). Contrasting with the *P. aeruginosa* strains tested, it was not susceptible to the 17mer derivative lacking N- and C-terminal amino acids (FIG. 4A). Thus, killing of *P. aeruginosa* and *S. pyogenes* by KRT6A-derivatives might involve different interactions between the peptides and bacterial cells, perhaps expected given the divergent cell wall structures of these pathogens.

Figure 4B:
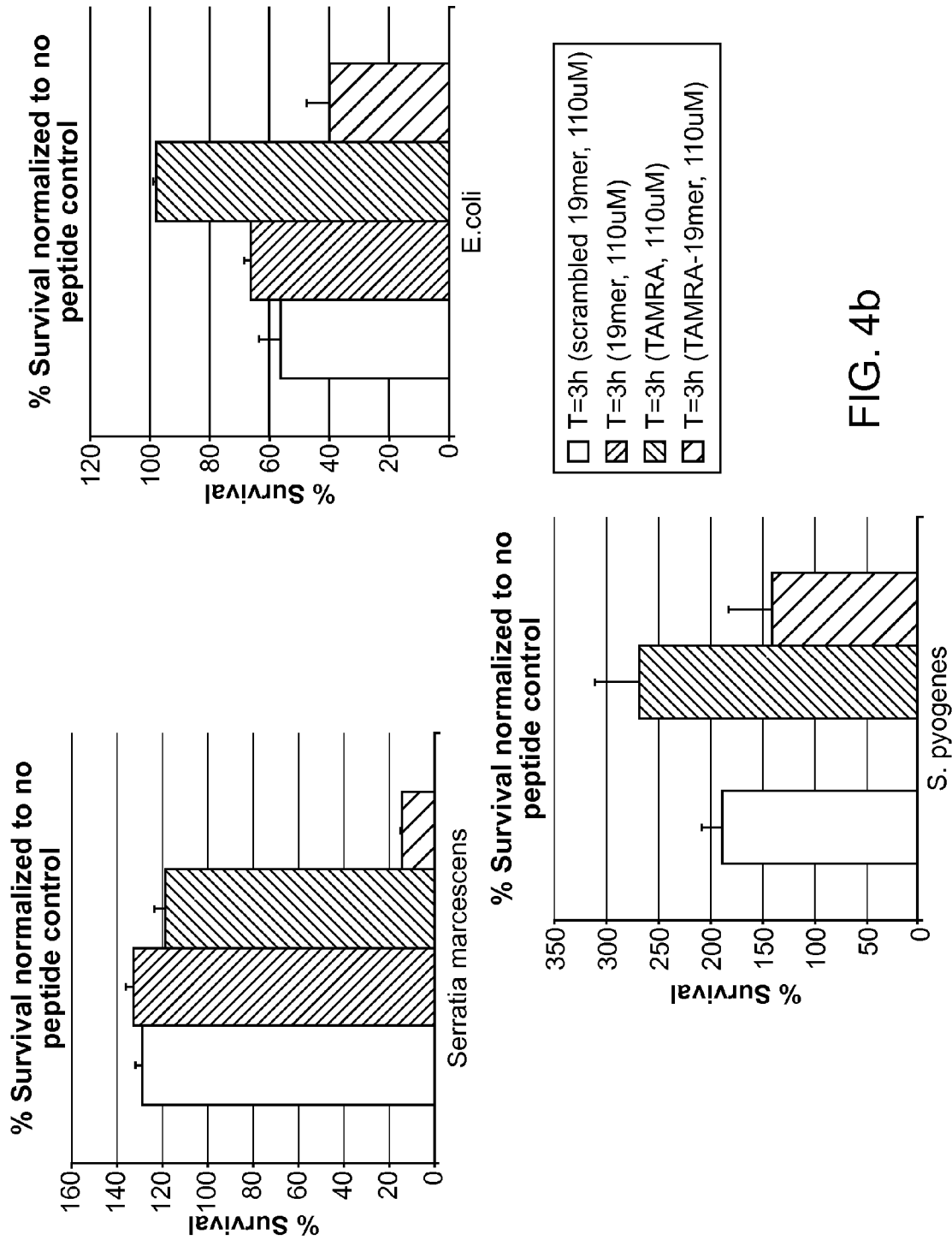

Not all of the microbes tested were susceptible to killing by the peptides tested. For example, neither the 19- nor the 17mer peptide was active against *Staphylococcus aureus, Staphylococcus epidermidis, Enterococcus faecalis, Escherichia coli, Candida albicans*, or *Serratia marcesens*. Interestingly, alterations to activity in were observed with TAMRA tagging. The TAMRA-tag enhanced the activity of the 19mer fragment against both *S. marcescens* and *E. coli* relative to unlabeled peptide ($P<0.005$) (FIG. 4B, left and middle panels). Mechanisms for enhanced activity with the tag are not clear, but one possibility is that these bacteria degrade or otherwise inactivate the peptides in a manner sterically hindered by the TAMRA fluorochrome analogous to inhibition of bacterial β-lactamase by semisynthetic β-lactam antibiotics (O'Callaghan C H, 1980 *Philos Trans R Soc Lond B Biol Sci.* 289:197-205). In contrast, the TAMRA-tag reduced (without completely abolishing) activity of the peptide against *S. pyogenes* ($P<0.005$) (FIG. 4B, right panel). Since TAMRA was attached to the N-terminal region, this might relate to why the shorter 17mer peptide that was missing an N-terminal arginine was also less effective against *S. pyogenes*. Whatever the mechanism, these results suggest structural modifications of KDAMPs might allow customized targeting of pathogens, of potential advantage in reducing adverse effects of antimicrobials or extending the antimicrobial spectrum and clinical potential of these molecules.

Paxiganan, another endogenous antimicrobial peptide (Ge Y et al., 1999 *Antimicrob Agents Chemother.* 43:782-788), has been found involved in selecting resident microbial flora. Related to this, it is of interest that *P. aeruginosa* and *S. pyogenes*, both extremely damaging to epithelia during infection, were killed by KDAMPs tested in this study, while the not-susceptible microbes tested are each considered part of the normal microbiota of one or more epithelial-lined tissue site. Further studies would be required to determine if keratin fragments can play a role in selecting resident microbiota. Considering that the rationale for diversity of keratins is not well understood, and that both keratins and microbiota tend to vary among different tissue sites and species, this is an area worth further exploration.

FIG. 4A and FIG. 4B: Spectrum of activity of keratin 6A-derived 19mer. (FIG. 4A) the 19mer KRT6A-derived peptide showed even greater bactericidal activity against *S. pyogenes* than *P. aeruginosa* (200 µg/mL, 3 h), but activity was lost with removal of C- and N-terminal amino acids from 19mer (17mer peptide). Other microbes tested were found not susceptible, or minimally susceptible. (FIG. 4B) TAMRA fluorochrome labeling of 19mer enhanced bactericidal activity against *S. marcescens* and *E. coli*, but lessened activity against *S. pyogenes* (all $P<0.005$ compared to 19mer). Activity against *S. pyogenes* remained statistically significant even with the TAMRA tag ($P<0.01$ compared to TAMRA alone).

While expression of keratin 6A reported in this study was constitutive, highly related isoforms of keratin 6 protein can be inducible, e.g. by injury (Takahashi K and Coulombe P A, 1997 *J Biol. Chem.* 272-11979-11985). The constant and rapid manner in which full-length keratin subunit proteins are released from their filamentous assembly (Kolsch A et al., 2010 *J Cell Sci.* 123:2266-2272) could support cellular demand for antimicrobial peptides to help defend against microbial pathogens. Interestingly, the overlapping sequences of the KRT6A-fragment family members suggested that proteolytic fragmentation of one peptide could still render another functional peptide, thus overcoming a common mechanism for inactivation of many antimicrobial peptides.

In sum, small peptide fragments derived from human keratin 6A possess bactericidal activity against at least two divergent human pathogens, *P. aeruginosa* and *S. pyogenes*.

REFERENCES

1. Krushna Padhi, B., Akimenko, M. A. & Ekker, M. Independent expansion of the keratin gene family in teleostean fish and mammals: an insight from phylogenetic analysis and radiation hybrid mapping of keratin genes in zebrafish. Gene. 368, 37-45 (2006).
2. Moll, R., Divo, M. & Langbein, L. The human keratins: biology and pathology. Histochem Cell Biol. 129, 705-33 (2008).
3. Jones, R. N. Microbial etiologies of hospital-acquired bacterial pneumonia and ventilator-associated bacterial pneumonia. Clin Infect Dis. 51 Suppl 1, S81-7 (2010).
4. Factor, S. H., Levine, O. S., Schwartz, B., Harrison, L. H., Farley, M. M., McGeer, A. & Schuchat, A. Invasive group A streptococcal disease: risk factors for adults. Emerg Infect Dis. 9, 970-7 (2003).
5. Tlaskalova-Hogenova, H., Stepankova, R., Hudcovic, T., Tuckova, L., Cukrowska, B., Lodinova-Zadnikova, R., Kozakova, H., Rossmann, P., Bartova, J., Sokol, D., Funda, D. P., Borovska, D., Rehakova, Z., Sinkora, J., Hofman, J., Drastich, P. & Kokesova, A. Commensal bacteria (normal microflora), mucosal immunity and chronic inflammatory and autoimmune diseases. Immunol Lett. 93, 97-108 (2004).
6. Tam, A., Wadsworth, S., Dorscheid, D., Man, S. P. & Sin, D. D. The airway epithelium: more than just a structural barrier. Ther Adv Respir Dis. (2011).
7. Karantza, V. Keratins in health and cancer: more than mere epithelial cell markers. Oncogene. 30, 127-38 (2011).
8. Raja, Sivamani, K., Garcia, M. S. & Isseroff, R. R. Wound re-epithelialization: modulating keratinocyte migration in wound healing. Front Biosci. 12, 2849-68 (2007).
9. Arin, M. J. The molecular basis of human keratin disorders. Hum Genet. 125, 355-73 (2009).
10. Stapleton, F., Keay, L., Edwards, K., Naduvilath, T., Dart, J. K., Brian, G. & Holden, B. A. The incidence of contact lens-related microbial keratitis in Australia. Ophthalmology. 115, 1655-62 (2008).
11. Keay, L., Edwards, K., Naduvilath, T., Taylor, H. R., Snibson, G. R., Forde, K. & Stapleton, F. Microbial keratitis predisposing factors and morbidity. Ophthalmology. 113, 109-16 (2006).
12. Mun, J. J., Tam, C., Kowbel, D., Hawgood, S., Barnett, M. J., Evans, D. J. & Fleiszig, S. M. Clearance of *Pseudomonas aeruginosa* from a healthy ocular surface involves surfactant protein D and is compromised by bacterial elastase in a murine null-infection model. Infect Immun. 77, 2392-8 (2009).
13. Ramphal, R., McNiece, M. T. & Polack, F. M. Adherence of *Pseudomonas aeruginosa* to the injured cornea: a step in the pathogenesis of corneal infections. Ann Ophthalmol. 13, 421-5 (1981).
14. Augustin, D. K., Heimer, S. R., Tam, C., Li, W. Y., Le Due, J. M., Evans, D. J. & Fleiszig, S. M. Role of defensins in corneal epithelial barrier function against *Pseudomonas aeruginosa* traversal. Infect Immun. 79, 595-605 (2011).
15. McDermott, A. M. The role of antimicrobial peptides at the ocular surface. Ophthalmic Res. 41, 60-75 (2009).
16. Zasloff, M. Antimicrobial peptides of multicellular organisms. Nature. 415, 389-95 (2002).
17. Leptihn, S., Har, J. Y., Wohland, T. & Ding, J. L. Correlation of charge, hydrophobicity, and structure with antimicrobial activity of S1 and MIRIAM peptides. Biochemistry. 49, 9161-70 (2010).
18. Gautier, R., Douguet, D., Antonny, B. & Drin, G. HELIQUEST: a web server to screen sequences with specific alpha-helical properties. Bioinformatics. 24, 2101-2 (2008).
19. Petersen, B., Petersen, T. N., Andersen, P., Nielsen, M. & Lundegaard, C. A generic method for assignment of reliability scores applied to solvent accessibility predictions. BMC Struct Biol. 9, 51 (2009).
20. Hofmann, K. & Stoffel, W. TMbase—A database of membrane spanning proteins segments. Biol. Chem. Hoppe-Seyler. 374, (1993).
21. Reynolds, N. L., De Cecco, M., Taylor, K., Stanton, C., Kilanowski, F., Kalapothakis, J., Seo, E., Uhrin, D., Campopiano, D., Govan, J., Macmillan, D., Barran, P. & Dorin, J. R. Peptide fragments of a beta-defensin derivative with potent bactericidal activity. Antimicrob Agents Chemother. 54, 1922-9 (2010).
22. Yeaman, M. R. & Yount, N. Y. Mechanisms of antimicrobial peptide action and resistance. Pharmacol Rev. 55, 27-55 (2003).
23. Coyne, M. J., Jr., Russell, K. S., Coyle, C. L. & Goldberg, J. B. The *Pseudomonas aeruginosa* algC gene encodes phosphoglucomutase, required for the synthesis of a complete lipopolysaccharide core. J Bacteriol. 176, 3500-7 (1994).
24. O'Callaghan, C. H. Structure-activity relations and beta-lactamase resistance. Philos Trans R Soc Lond B Biol Sci. 289, 197-205 (1980).
25. Ge, Y., MacDonald, D. L., Holroyd, K. J., Thornsberry, C., Wexler, H. & Zasloff, M. In vitro antibacterial properties of pexiganan, an analog of magainin. Antimicrob Agents Chemother. 43, 782-8 (1999).
26. Takahashi, K. & Coulombe, P. A. Defining a region of the human keratin 6a gene that confers inducible expression in stratified epithelia of transgenic mice. J Biol Chem. 272, 11979-85 (1997).
27. Kolsch, A., Windoffer, R., Wurflinger, T., Aach, T. & Leube, R. E. The keratin-filament cycle of assembly and disassembly. J Cell Sci. 123, 2266-72 (2010).
28. Robertson, D. M., Li, L., Fisher, S., Pearce, V. P., Shay, J. W., Wright, W. E., Cavanagh, H. D. & Jester, J. V. Characterization of growth and differentiation in a telomerase-immortalized human corneal epithelial cell line. Invest Ophthalmol Vis Sci. 46, 470-8 (2005).
29. Rowe, P. S. & Meadow, P. M. Structure of the Core oligosaccharide from the lipopolysaccharide of *Pseudomonas aeruginosa* PAC1R and its defective mutants. Eur J Biochem. 132, 329-37 (1983).
30. Eng, J. K., MacCormak, A. L. & Yates, J. R., 3rd. An approach to correlate tandem mass spectral data of peptides with amino acid sequences in a protein database. J. Am. Soc. Mass Spectrom. 5, 976-989 (1994).
31. Tabb, D. L., McDonald, W. H. & Yates, J. R., 3rd. DTA-Select and Contrast: tools for assembling and comparing protein identifications from shotgun proteomics. J Proteome Res. 1, 21-6 (2002).

Example 2

Phosphorylation of KDAMPs Increases Bactericidal Activity

Synthetic 19-mer KDAMP peptides were synthesized with or without tyrosine phosphorylation. The bactericidal effect of the peptides was compared.

RAIGGGLSSVGGGSSTIKY (SEQ ID NO:6) (non-phosphorylated 19-mer);

RAIGGGLSSVGGGSSTIK(phospho-Y) (SEQ ID NO:62) (phosphorylated 19-mer).

Figure 6:
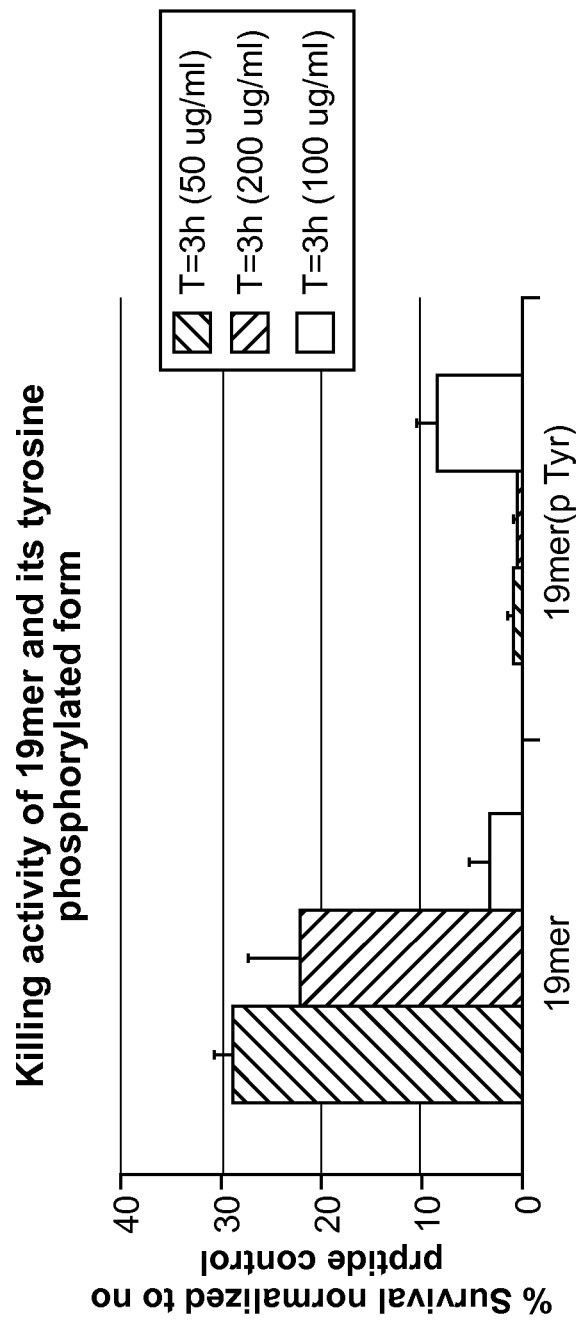
FIG. 6 depicts bactericidal activity of a keratin 6A-derived 19-mer with a phosphorylated Tyr reside compared to that of the non-phosphorylated 19-mer.

As shown in FIG. 6, the phosphorylated 19-mer exhibited significantly increased bactericidal activity compared with the non-phosphorylated 19-mer.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising:
   a) an antimicrobial peptide, wherein the peptide has a length of from 10 amino acids to 50 amino acids, and wherein the peptide comprises an amino acid sequence having at least 95% amino acid sequence identity to a contiguous stretch of from 10 amino acids to 35 amino acids of the sequence

```
                                           (SEQ ID NO: 63)
   YSYGSGLGVGGGFSSSSGRAIGGGLSSVGGGSSTIKYTTTSSSSR,
   ``` wherein the peptide contains at least one phosphorylated tyrosine residue, and
   b) a surfactant.

2. The antimicrobial peptide of claim 1, wherein the peptide comprises an amino acid sequence selected from:

```
                           (SEQ ID NO: 1)
   AIGGGLSSVGGGSSTIK;

(SEQ ID NO: 2)
   AIGGGLSSVGGGSSTIKY;

(SEQ ID NO: 3)
   RAIGGGLSSVGGGSSTIK;

(SEQ ID NO: 4)
   GGLSSVGGGSSTIK;

(SEQ ID NO: 5)
   AIGGGLSSVGGGS;

(SEQ ID NO: 6)
   RAIGGGLSSVGGGSSTIKY;

(SEQ ID NO: 7)
   ygsglgvgggfssssgraiggglssvgggsstiky;

(SEQ ID NO: 8)
   YGSGLGVGGGFSSSSGRAIGGGLSSVGGGSSTIKYT;
   and (SEQ ID NO: 9)
   GGLSSVGGGS.
   ```

3. The antimicrobial peptide of claim 1, wherein at least two adjacent amino acids of the peptide are joined via a linkage other than an amide bond.

4. The composition of claim 1, wherein the antimicrobial peptide is present in an amount of from 0.5 weight % to 20 weight %.

5. The composition of claim 1, further comprising one or more agents selected from the group consisting of a pH adjusting agent, a dye, a fragrance, and a complexing agent.

6. The composition of claim 1, wherein the composition is a solid, a liquid, or a gel.

7. A pharmaceutical formulation comprising:
   a) the composition of claim 1; and
   b) a pharmaceutically acceptable excipient.

8. The composition of claim 1, wherein the surfactant is a nonionic surfactant.

9. The composition of claim 1, wherein the surfactant is an amphoteric surfactant.

10. The composition of claim 1, wherein the surfactant is an anionic surfactant.

11. The composition of claim 1, wherein the surfactant is a cationic surfactant.

12. The composition of claim 1, wherein the peptide comprises an amino acid sequence having at least 98% amino acid sequence identity to a contiguous stretch of from 10 amino acids to 35 amino acids of the sequence YSYGSGLGVGGG-FSSSSGRAIGGGLSSVGGGSSTIKYTTTSSSSR (SEQ ID NO:63).

13. The composition of claim 1, wherein the peptide comprises an amino acid sequence having at least 99% amino acid sequence identity to a contiguous stretch of from 10 amino acids to 35 amino acids of the sequence YSYGSGLGVGGG-FSSSSGRAIGGGLSSVGGGSSTIKYTTTSSSSR (SEQ ID NO:63).

14. A method of inhibiting growth of a bacterium, the method comprising contacting the bacterium with a growth inhibiting amount of an antimicrobial peptide, wherein the peptide has a length of from 10 amino acids to 50 amino acids, and wherein the peptide comprises an amino acid sequence having at least 95% amino acid sequence identity to a contiguous stretch of from 10 amino acids to 35 amino acids of the sequence YSYGSGLGVGGGFSSSSGRAIGGGLSS-VGGGSSTIKYTTTSSSSR (SEQ ID NO:63), wherein the peptide contains at least one phosphorylated tyrosine residue.

15. The method of claim 14, wherein said contacting is carried out in vitro.

16. The method of claim 15, wherein the bacterium is on the surface of a medical device.

17. The method of claim 15, wherein the bacterium is on a hard surface in a healthcare facility, an educational facility, a detention facility, or a residence.

18. The method of claim 14, wherein the bacterium is in a liquid.

19. The method of claim 14, wherein said contacting is in vivo.

20. A method of treating a bacterial infection in an individual in need thereof, the method comprising administering to the individual an effective amount of an antimicrobial peptide, wherein the peptide has a length of from 10 amino acids to 50 amino acids, and wherein the peptide comprises an amino acid sequence having at least 95% amino acid sequence identity to a contiguous stretch of from 10 amino acids to 35 amino acids of the sequence YSYGSGLGVGGG-FSSSSGRAIGGGLSSVGGGSSTIKYTTTSSSSR (SEQ ID NO:63), wherein the peptide contains at least one phosphorylated tyrosine residue.

* * * * *

SEQUENCE LISTING

<160> NUMBER OF SEQ ID NOS: 73

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Ala Ile Gly Gly Gly Leu Ser Ser Val Gly Gly Gly Ser Ser Thr Ile
1               5                   10                  15

Lys

<210> SEQ ID NO 2
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 2

Ala Ile Gly Gly Gly Leu Ser Ser Val Gly Gly Gly Ser Ser Thr Ile
1               5                   10                  15

Lys Tyr

<210> SEQ ID NO 3
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 3

Arg Ala Ile Gly Gly Gly Leu Ser Ser Val Gly Gly Gly Ser Ser Thr
1               5                   10                  15

Ile Lys

<210> SEQ ID NO 4
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 4

Gly Gly Leu Ser Ser Val Gly Gly Gly Ser Ser Thr Ile Lys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 5

Ala Ile Gly Gly Gly Leu Ser Ser Val Gly Gly Gly Ser
1               5                   10

<210> SEQ ID NO 6
<211> LENGTH: 19
<212> TYPE: PRT
<213> ORGANISM: Artificial Sequence
<220> FEATURE:

<223> OTHER INFORMATION: Synthetic Peptide

<400> SEQUENCE: 6

Arg Ala Ile Gly Gly Gly Leu Ser Ser Val Gly Gly Gly Ser Ser Thr
1               5                   10                  15

Ile Lys Tyr

<210> SEQ ID NO 7
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 7

Tyr Gly Ser Gly Leu Gly Val Gly Gly Gly Phe Ser Ser Ser Ser Gly
1               5                   10                  15

Arg Ala Ile Gly Gly Gly Leu Ser Ser Val Gly Gly Gly Ser Ser Thr
                20                  25                  30

Ile Lys Tyr
        35

<210> SEQ ID NO 8
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 8

Tyr Gly Ser Gly Leu Gly Val Gly Gly Gly Phe Ser Ser Ser Ser Gly
1               5                   10                  15

Arg Ala Ile Gly Gly Gly Leu Ser Ser Val Gly Gly Gly Ser Ser Thr
                20                  25                  30

Ile Lys Tyr Thr
        35

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 9

Gly Gly Leu Ser Ser Val Gly Gly Gly Ser
1               5                   10

<210> SEQ ID NO 10
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 10

Gly Ser Gly Leu Gly Val Gly Gly Gly Phe Ser Ser Ser Ser Gly Arg
1               5                   10                  15

Ala Ile Gly Gly Gly Leu Ser Ser Val Gly Gly Gly Ser Ser Thr Ile
                20                  25                  30

Lys

```
<210> SEQ ID NO 11
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 11

Gly Ser Gly Leu Gly Val Gly Gly Phe Ser Ser Ser Gly Arg
1               5                   10                  15

Ala Ile Gly Gly Gly Leu Ser Ser Val Gly Gly Ser Ser Thr Ile
            20                  25                  30

Lys Tyr

<210> SEQ ID NO 12
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 12

Ser Gly Leu Gly Val Gly Gly Gly Phe Ser Ser Ser Gly Arg Ala
1               5                   10                  15

Ile Gly Gly Gly Leu Ser Ser Val Gly Gly Ser Ser Thr Ile Lys
            20                  25                  30

<210> SEQ ID NO 13
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 13

Ser Gly Leu Gly Val Gly Gly Gly Phe Ser Ser Ser Gly Arg Ala
1               5                   10                  15

Ile Gly Gly Gly Leu Ser Ser Val Gly Gly Ser Ser Thr Ile Lys
            20                  25                  30

Tyr

<210> SEQ ID NO 14
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 14

Gly Leu Gly Val Gly Gly Gly Phe Ser Ser Ser Gly Arg Ala Ile
1               5                   10                  15

Gly Gly Gly Leu Ser Ser Val Gly Gly Ser Ser Thr Ile Lys
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 15

Gly Leu Gly Val Gly Gly Gly Phe Ser Ser Ser Gly Arg Ala Ile
1               5                   10                  15
```

Gly Gly Gly Leu Ser Ser Val Gly Gly Gly Ser Ser Thr Ile Lys Tyr
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 16

Leu Gly Val Gly Gly Gly Phe Ser Ser Ser Gly Arg Ala Ile Gly
1               5                   10                  15

Gly Gly Leu Ser Ser Val Gly Gly Ser Ser Thr Ile Lys
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 17

Leu Gly Val Gly Gly Gly Phe Ser Ser Ser Gly Arg Ala Ile Gly
1               5                   10                  15

Gly Gly Leu Ser Ser Val Gly Gly Ser Ser Thr Ile Lys Tyr
            20                  25                  30

<210> SEQ ID NO 18
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 18

Gly Val Gly Gly Gly Phe Ser Ser Ser Gly Arg Ala Ile Gly Gly
1               5                   10                  15

Gly Leu Ser Ser Val Gly Gly Ser Ser Thr Ile Lys
            20                  25

<210> SEQ ID NO 19
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 19

Gly Val Gly Gly Gly Phe Ser Ser Ser Gly Arg Ala Ile Gly Gly
1               5                   10                  15

Gly Leu Ser Ser Val Gly Gly Ser Ser Thr Ile Lys Tyr
            20                  25                  30

<210> SEQ ID NO 20
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 20

Val Gly Gly Gly Phe Ser Ser Ser Ser Gly Arg Ala Ile Gly Gly Gly

```
1               5                   10                  15
Leu Ser Ser Val Gly Gly Gly Ser Ser Thr Ile Lys
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 21

Val Gly Gly Gly Phe Ser Ser Ser Gly Arg Ala Ile Gly Gly Gly
1               5                   10                  15

Leu Ser Ser Val Gly Gly Gly Ser Ser Thr Ile Lys Tyr
            20                  25

<210> SEQ ID NO 22
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 22

Gly Gly Gly Phe Ser Ser Ser Gly Arg Ala Ile Gly Gly Gly Leu
1               5                   10                  15

Ser Ser Val Gly Gly Gly Ser Ser Thr Ile Lys
            20                  25

<210> SEQ ID NO 23
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 23

Gly Gly Gly Phe Ser Ser Ser Gly Arg Ala Ile Gly Gly Gly Leu
1               5                   10                  15

Ser Ser Val Gly Gly Gly Ser Ser Thr Ile Lys Tyr
            20                  25

<210> SEQ ID NO 24
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 24

Leu Pro Gly Val Ser Arg Ser Gly Phe Ser Ser
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 25

Gly Val Ser Arg Ser Gly Phe Ser Ser Val Ser Val Ser Arg
1               5                   10
```

```
<210> SEQ ID NO 26
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 26

Ser Gly Phe Ser Ser Val Ser Val Ser Arg
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 27

Ser Gly Phe Ser Ser Val Ser Val Ser Arg Ser
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 28

Ser Arg Gly Ser Gly Gly Leu Gly Gly Ala Cys Gly Gly Ala Gly Phe
1               5                   10                  15

Gly Ser

<210> SEQ ID NO 29
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 29

Gly Ser Gly Gly Leu Gly Gly Ala Cys Gly Gly Ala Gly Phe Gly Ser
1               5                   10                  15

<210> SEQ ID NO 30
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 30

Gly Gly Ala Gly Phe Gly Ser Arg Ser Leu Tyr Gly Leu Gly Gly Ser
1               5                   10                  15

Lys

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 31
```

Ser Leu Tyr Gly Leu Gly Gly Ser Lys Arg Ile Ser Ile Gly Gly
1               5                   10                  15

<210> SEQ ID NO 32
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 32

Ser Leu Tyr Gly Leu Gly Gly Ser Lys Arg Ile Ser Ile Gly Gly
1               5                   10                  15

Ser

<210> SEQ ID NO 33
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 33

Ala Gly Gly Ser Tyr Gly Phe Gly Gly Ala Gly Ser Gly Phe Gly
1               5                   10                  15

<210> SEQ ID NO 34
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 34

Ala Gly Gly Ser Tyr Gly Phe Gly Gly Ala Gly Ser Gly Phe Gly Phe
1               5                   10                  15

Gly Gly Gly Ala
            20

<210> SEQ ID NO 35
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 35

Arg Asn Leu Asp Leu Asp Ser Ile Ile Ala Glu Val Lys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 36

Asn Leu Asp Leu Asp Ser Ile Ile Ala Glu Val Lys
1               5                   10

<210> SEQ ID NO 37
<211> LENGTH: 19
<212> TYPE: PRT
<213> ORGANISM: Artificial Sequence
<220> FEATURE:

<223> OTHER INFORMATION: Synthetic Peptide

<400> SEQUENCE: 37

Tyr Ser Tyr Gly Ser Gly Leu Gly Val Gly Gly Gly Phe Ser Ser Ser
1               5                   10                  15

Ser Gly Arg

<210> SEQ ID NO 38
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 38

Tyr Ser Tyr Gly Ser Gly Leu Gly Val Gly Gly Gly Phe Ser Ser Ser
1               5                   10                  15

Ser Gly Arg Ala Ile Gly Gly Gly Leu Ser Ser Val Gly Gly Gly Ser
            20                  25                  30

Ser Thr Ile Lys
        35

<210> SEQ ID NO 39
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 39

Ser Tyr Gly Ser Gly Leu Gly Val Gly Gly Gly Phe Ser Ser Ser Ser
1               5                   10                  15

Gly Arg

<210> SEQ ID NO 40
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 40

Tyr Gly Ser Gly Leu Gly Val Gly Gly Gly Phe Ser Ser Ser Ser Gly
1               5                   10                  15

Arg

<210> SEQ ID NO 41
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 41

Tyr Gly Ser Gly Leu Gly Val Gly Gly Gly Phe Ser Ser Ser Ser Gly
1               5                   10                  15

Arg Ala Ile Gly Gly Gly Leu Ser Ser Val Gly Gly Gly Ser Ser Thr
            20                  25                  30

Ile Lys

<210> SEQ ID NO 42
<211> LENGTH: 16

```
<212> TYPE: PRT
<213> ORGANISM: Artificial Sequence
<220> FEATURE:
<223> OTHER INFORMATION: Synthetic Peptide

<400> SEQUENCE: 42

Gly Ser Gly Leu Gly Val Gly Gly Gly Phe Ser Ser Ser Ser Gly Arg
1               5                   10                  15

<210> SEQ ID NO 43
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 43

Gly Gly Phe Ser Ser Ser Ser Gly Arg Ala Ile Gly Gly Gly Leu Ser
1               5                   10                  15

Ser Val Gly Gly Gly Ser Ser Thr Ile Lys
            20                  25

<210> SEQ ID NO 44
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 44

Phe Ser Ser Ser Ser Gly Arg Ala Ile Gly Gly Gly Leu Ser Ser Val
1               5                   10                  15

Gly Gly Gly Ser Ser Thr Ile Lys
            20

<210> SEQ ID NO 45
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 45

Ser Ser Ser Ser Gly Arg Ala Ile Gly Gly Gly Leu Ser Ser Val Gly
1               5                   10                  15

Gly Gly Ser Ser Thr Ile Lys
            20

<210> SEQ ID NO 46
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 46

Ser Ser Ser Gly Arg Ala Ile Gly Gly Gly Leu Ser Ser Val Gly Gly
1               5                   10                  15

Gly Ser Ser Thr Ile Lys
            20

<210> SEQ ID NO 47
<211> LENGTH: 21
<212> TYPE: PRT
<213> ORGANISM: Artificial Sequence
```

<220> FEATURE:
<223> OTHER INFORMATION: Synthetic Peptide

<400> SEQUENCE: 47

Ser Ser Gly Arg Ala Ile Gly Gly Gly Leu Ser Ser Val Gly Gly Gly
1               5                   10                  15

Ser Ser Thr Ile Lys
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 48

Ser Gly Arg Ala Ile Gly Gly Gly Leu Ser Ser Val Gly Gly Gly Ser
1               5                   10                  15

Ser Thr Ile Lys
            20

<210> SEQ ID NO 49
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 49

Gly Arg Ala Ile Gly Gly Gly Leu Ser Ser Val Gly Gly Gly Ser Ser
1               5                   10                  15

Thr Ile Lys

<210> SEQ ID NO 50
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 50

Ala Ile Gly Gly Gly Leu Ser Ser Val Gly Gly Gly Ser Ser
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 51

Ala Ile Gly Gly Gly Leu Ser Ser Val Gly Gly Gly Ser Ser Thr
1               5                   10                  15

<210> SEQ ID NO 52
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 52

Ala Ile Gly Gly Gly Leu Ser Ser Val Gly Gly Gly Ser Ser Thr Ile

```
1               5                   10                  15

Lys Tyr

<210> SEQ ID NO 53
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 53

Ala Ile Gly Gly Gly Leu Ser Ser Val Gly Gly Ser Ser Thr Ile
1               5                   10                  15

Lys Tyr Thr

<210> SEQ ID NO 54
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 54

Ile Gly Gly Gly Leu Ser Ser Val Gly Gly Ser Ser Thr Ile Lys
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 55

Gly Gly Gly Leu Ser Ser Val Gly Gly Ser Ser Thr Ile Lys
1               5                   10                  15

<210> SEQ ID NO 56
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 56

Val Gly Gly Gly Ser Ser Thr Ile Lys Tyr Thr Thr Thr Ser Ser Ser
1               5                   10                  15

Ser Arg

<210> SEQ ID NO 57
<211> LENGTH: 564
<212> TYPE: PRT
<213> ORGANISM: Homo sapiens

<400> SEQUENCE: 57

Met Ala Ser Thr Ser Thr Thr Ile Arg Ser His Ser Ser Ser Arg Arg
1               5                   10                  15

Gly Phe Ser Ala Asn Ser Ala Arg Leu Pro Gly Val Ser Arg Ser Gly
                20                  25                  30

Phe Ser Ser Val Ser Val Ser Arg Ser Arg Gly Ser Gly Gly Leu Gly
            35                  40                  45

Gly Ala Cys Gly Gly Ala Gly Phe Gly Ser Arg Ser Leu Tyr Gly Leu
        50                  55                  60
```

```
Gly Gly Ser Lys Arg Ile Ser Ile Gly Gly Ser Cys Ala Ile Ser
 65                  70                  75                  80

Gly Gly Tyr Gly Ser Arg Ala Gly Gly Ser Tyr Gly Phe Gly Gly Ala
                 85                  90                  95

Gly Ser Gly Phe Gly Phe Gly Gly Ala Gly Ile Gly Phe Gly Leu
            100                 105                 110

Gly Gly Gly Ala Gly Leu Ala Gly Gly Phe Gly Gly Pro Gly Phe Pro
            115                 120                 125

Val Cys Pro Pro Gly Gly Ile Gln Glu Val Thr Val Asn Gln Ser Leu
    130                 135                 140

Leu Thr Pro Leu Asn Leu Gln Ile Asp Pro Thr Ile Gln Arg Val Arg
145                 150                 155                 160

Ala Glu Glu Arg Glu Gln Ile Lys Thr Leu Asn Asn Lys Phe Ala Ser
                165                 170                 175

Phe Ile Asp Lys Val Arg Phe Leu Glu Gln Gln Asn Lys Val Leu Glu
            180                 185                 190

Thr Lys Trp Thr Leu Leu Gln Glu Gln Gly Thr Lys Thr Val Arg Gln
            195                 200                 205

Asn Leu Glu Pro Leu Phe Glu Gln Tyr Ile Asn Asn Leu Arg Arg Gln
210                 215                 220

Leu Asp Ser Ile Val Gly Glu Arg Gly Arg Leu Asp Ser Glu Leu Arg
225                 230                 235                 240

Gly Met Gln Asp Leu Val Glu Asp Phe Lys Asn Lys Tyr Glu Asp Glu
                245                 250                 255

Ile Asn Lys Arg Thr Ala Ala Glu Asn Glu Phe Val Thr Leu Lys Lys
            260                 265                 270

Asp Val Asp Ala Ala Tyr Met Asn Lys Val Glu Leu Gln Ala Lys Ala
            275                 280                 285

Asp Thr Leu Thr Asp Glu Ile Asn Phe Leu Arg Ala Leu Tyr Asp Ala
            290                 295                 300

Glu Leu Ser Gln Met Gln Thr His Ile Ser Asp Thr Ser Val Val Leu
305                 310                 315                 320

Ser Met Asp Asn Asn Arg Asn Leu Asp Leu Asp Ser Ile Ile Ala Glu
                325                 330                 335

Val Lys Ala Gln Tyr Glu Glu Ile Ala Gln Arg Ser Arg Ala Glu Ala
            340                 345                 350

Glu Ser Trp Tyr Gln Thr Lys Tyr Glu Glu Leu Gln Val Thr Ala Gly
            355                 360                 365

Arg His Gly Asp Asp Leu Arg Asn Thr Lys Gln Glu Ile Ala Glu Ile
            370                 375                 380

Asn Arg Met Ile Gln Arg Leu Arg Ser Glu Ile Asp His Val Lys Lys
385                 390                 395                 400

Gln Cys Ala Asn Leu Gln Ala Ala Ile Ala Asp Ala Glu Gln Arg Gly
                405                 410                 415

Glu Met Ala Leu Lys Asp Ala Lys Asn Lys Leu Glu Gly Leu Glu Asp
            420                 425                 430

Ala Leu Gln Lys Ala Lys Gln Asp Leu Ala Arg Leu Leu Lys Glu Tyr
            435                 440                 445

Gln Glu Leu Met Asn Val Lys Leu Ala Leu Asp Val Glu Ile Ala Thr
            450                 455                 460

Tyr Arg Lys Leu Leu Glu Gly Glu Glu Cys Arg Leu Asn Gly Glu Gly
465                 470                 475                 480
```

```
Val Gly Gln Val Asn Ile Ser Val Val Gln Ser Thr Val Ser Ser Gly
            485                 490                 495

Tyr Gly Ala Ser Gly Val Gly Ser Gly Leu Gly Leu Gly Gly Gly
        500                 505                 510

Ser Ser Tyr Ser Tyr Gly Ser Gly Leu Gly Val Gly Gly Phe Ser
            515                 520                 525

Ser Ser Ser Gly Arg Ala Ile Gly Gly Gly Leu Ser Ser Val Gly Gly
530                 535                 540

Gly Ser Ser Thr Ile Lys Tyr Thr Thr Thr Ser Ser Ser Arg Lys
545                 550                 555                 560

Ser Tyr Lys His

<210> SEQ ID NO 58
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 58
cgaaggcguu ggacaaguc                                              19

<210> SEQ ID NO 59
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 59
gaacaagguu gaacugcaa                                              19

<210> SEQ ID NO 60
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 60 gcaguccac caucaagua                                               19

<210> SEQ ID NO 61
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 61
gagaucaacu uccugagag                                              19

<210> SEQ ID NO 62
<211> LENGTH: 19
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (19)..(19)
<223> OTHER INFORMATION: phosphorylated Y

<400> SEQUENCE: 62
```

```
Arg Ala Ile Gly Gly Gly Leu Ser Ser Val Gly Gly Ser Ser Thr
1               5                   10                  15

Ile Lys Tyr
```

<210> SEQ ID NO 63
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 63

```
Tyr Ser Tyr Gly Ser Gly Leu Gly Val Gly Gly Gly Phe Ser Ser
1               5                   10                  15

Ser Gly Arg Ala Ile Gly Gly Gly Leu Ser Ser Val Gly Gly Ser
                20                  25                  30

Ser Thr Ile Lys Tyr Thr Thr Thr Ser Ser Ser Arg
                35                  40                  45
```

<210> SEQ ID NO 64
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 64

```
Ala Gly Gly Ile Val Ile
1               5
```

<210> SEQ ID NO 65
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 65

```
Ala Gly Gly Ile Val Ile Ser Leu Lys Gly Gly Ser Ser Tyr Gly Gly
1               5                   10                  15

Thr Ser
```

<210> SEQ ID NO 66
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 66

```
Ala Gly Gly Ile Val Ile Ser Leu Lys Gly Gly Ser Ser Arg Gly Gly
1               5                   10                  15

Thr Ser
```

<210> SEQ ID NO 67
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 67

```
Ala Gly Gly Ile Val Ile Ser Leu Lys Gly Gly Ser Ser Gly Gly Thr
1               5                   10                  15
```

Ser

<210> SEQ ID NO 68
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 68

Gly Gly Ile Val Ser Leu Lys Gly Ser Ser Gly Gly Thr Ser
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 69

Gly Gly Val Ile Ser Leu Gly Gly Ser Gly Gly Ser Ala
1               5                   10

<210> SEQ ID NO 70
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (14)..(14)
<223> OTHER INFORMATION: X=Y or R

<400> SEQUENCE: 70

Ala Gly Gly Ile Val Ile Ser Leu Lys Gly Gly Ser Ser Xaa Gly Gly
1               5                   10                  15

Thr Ser

<210> SEQ ID NO 71
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 71

Thr Gly Gly Ile Val Ile Ser Leu Lys Gly Gly Ser Ser Tyr Gly Gly
1               5                   10                  15

Thr Ser

<210> SEQ ID NO 72
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 72

Gly Ser Gly Tyr Ser Leu Gly Gly Gly Ser Gly Arg Gly Ser Ser Val
1               5                   10                  15

Ala Phe

```
<210> SEQ ID NO 73
<211> LENGTH: 10
<212> TYPE: PRT
<213> ORGANISM: Artificial Sequence
<220> FEATURE:
<223> OTHER INFORMATION: Synthetic peptide

<400> SEQUENCE: 73

Val Ser Leu Gly Ser Gly Gly Ser Gly Gly
1               5                   10
```